US007249006B2

(12) United States Patent
Lombardo et al.

(10) Patent No.: US 7,249,006 B2
(45) Date of Patent: Jul. 24, 2007

(54) METHOD AND SYSTEM FOR BIO-SURVEILLANCE DETECTION AND ALERTING

(75) Inventors: Joseph S. Lombardo, Annapolis, MD (US); Fernando J. Pineda, Baltimore, MD (US); Howard S. Burkom, Baltimore, MD (US); Bruce K. Newhall, Columbia, MD (US); Rashid A. Chotani, Owings Mills, MD (US); Richard A. Wojcik, Columbia, MD (US); Wayne A. Loschen, Odenton, MD (US)

(73) Assignee: The Johns Hopkins University, Baltimore, MD (US)

( * ) Notice: Subject to any disclaimer, the term of this patent is extended or adjusted under 35 U.S.C. 154(b) by 582 days.

(21) Appl. No.: 10/130,404

(22) PCT Filed: Mar. 23, 2001

(86) PCT No.: PCT/US01/09244

§ 371 (c)(1),
(2), (4) Date: May 15, 2002

(87) PCT Pub. No.: WO01/73616

PCT Pub. Date: Oct. 4, 2001

(65) Prior Publication Data

US 2003/0009239 A1 Jan. 9, 2003

Related U.S. Application Data

(60) Provisional application No. 60/191,576, filed on Mar. 23, 2000, provisional application No. 60/191,563, filed on Mar. 23, 2000.

(51) Int. Cl.
  *G06G 7/48* (2006.01)
(52) U.S. Cl. ............................................. 703/2; 703/11
(58) Field of Classification Search .................. 702/19
  See application file for complete search history.

(56) References Cited

U.S. PATENT DOCUMENTS 5,911,132 A 6/1999 Sloane

OTHER PUBLICATIONS

Nobre, Int'l J. Epidemiol., 23(2):408-418 (1994).*
Quenel, Eur. J. Epidemiol., 14:275-285 (1998).*
Glass, Amer. J. Public Health, 85(7):944-948 (1995).*
Merriam Webster On-line Dictionary: definition of relevant. Obtained from http://209.161.50/dictionary/relevent on Mar. 15, 2007.*
PCT International Search Report, PCT/US01/09244, mailed Oct. 8, 2002.
Infantosi A.F.C. et al: "Phase spectral analysis of measles epidemic outbreaks" MEDINFO 89. Proceedings of the Sixth Conference on Medical Informatics, Beijing, China and Singapore, Oct. 16-20, 1989 and Dec. 11-15, 1989, pp. 497-501, XP008007972E,1989, Amsterdam, Netherlands.
Nobre F. F: "Detecting abnormal patterns in public health surveillance data with a probability index function" MEDINFO 92. Proceedings of the Seventh World Congress on Medical Informatics, Geneva, Switzerland, Sep. 6-10, 1992, pp. 904-909 vol. 2, XP008007963 1992, Amsterdam, Netherlands.
Bailey N. T. J: "Macro-modelling and prediction of epidemic spread at community level" Mathematic Modelling, 1986, USA, vol. 7, No. 5-8, pp. 689-717, XP008007959.
Snacken R. et al: "The CARE Telematics network for the surveillance of influenza in Europe" Methods of Information in Medicine, Dec. 1995, F. K. Schattauer Verlagsgesellschaft, Germany, vol. 34, No. 5, pp. 518-522, XP008007965.

* cited by examiner

*Primary Examiner*—Marjorie A. Moran
(74) *Attorney, Agent, or Firm*—Albert J. Fasulo, II

(57) ABSTRACT

Background noise from relevant data sets, including for example over-the-counter sales data, absenteeism data, etc., is subtracted using a background estimation algorithm that outputs residual data. The effects of hypothetical anomalous events, such as a bio-terrorist attack, on the relevant data sets are modeled to create replica data. The replica data may be based on input from epidemiologists and various scenario templates including information on disease manifestation and other intelligence. The residual data and the replica data are then matched using a detector. Types of detectors include for example adaptive matched-filter detectors, change detectors and Bayesian Inference Networks. An alarm is triggered if a real anomalous event similar to a hypothetical anomalous event is detected. A Geographical Information System (GIS) may be used to display data from individual zip codes.

22 Claims, 21 Drawing Sheets

Fig. 1
Top Bio-Weapon Threats

| Agent | Type | Minimum Dose | Incubation period | Initial Symptoms | Duration of illness | Lethality | Animal Indicator |
|---|---|---|---|---|---|---|---|
| Anthrax | Bacteria | 8,000 (spores) | 1-6 days | Flu-like | 3-5 days | High 90% | Yes |
| Plague | Bacteria | 100 organisms | 2-3 days | Pneumonia / Flu-like | 1-6 days | High 90-100% | Yes |
| Tuleramia | Bacteria | 10 organisms | 2-10 days (avg. 3-5) | Flu-like | >=2 weeks | Moderate 5-30% | Yes |
| Brucellosis | Bacteria | 10 organisms | 5-60 days | Flu-like | Weeks to months | Low 2-10% | Yes |
| Q Fever | Rickettsia | 1 organisms | 10-40 days | Flu-like | 2-14 days | Low 4% | Yes |
| Smallpox | Virus | 10 organisms | 7-17 days (avg. 12) | Flu-like | 4 weeks | High 30% | Animal Variants |
| Encephalitides VEE, EEE, WEE | Virus | | | Flu-like | days to weeks | low | Yes |
| Hemorrhagic Fevers Ebola, Marburg | Virus | 1 organism | 4-21days | Flu-like | 7-16 days | High Marburg 25% Ebola 50-90% | Yes |
| Botulinum | Toxin | 100 ng | 1-5 days | muscle weakness | 24-72 hours | High 30% | Yes |

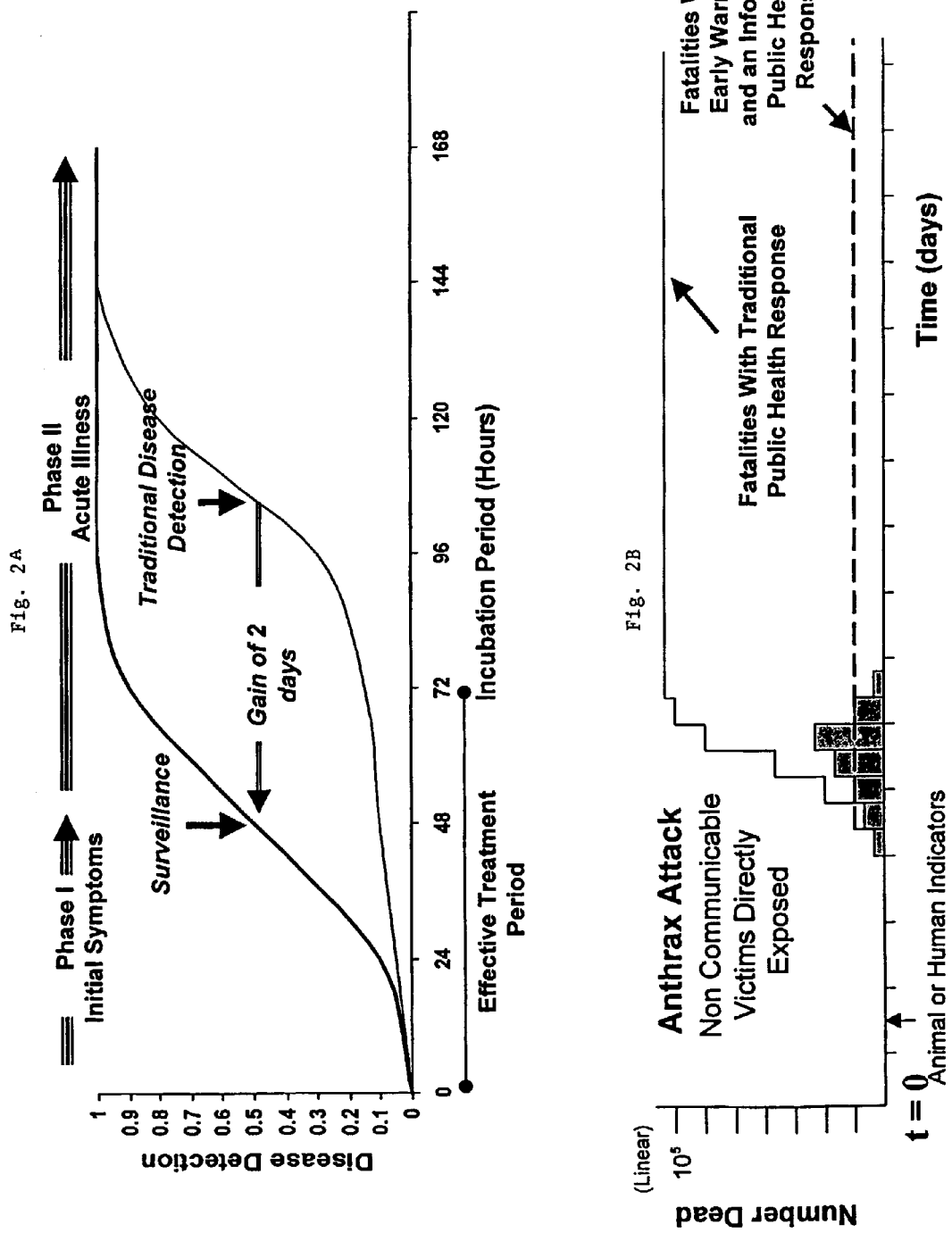

Fig. 5A Weekly Sales of Selected OTC Products

| Region Maps | Detector Outputs | Slide Show Control |
|---|---|---|
| ○ Region Status<br>○ Region Legend | Regions     Diseases<br>☐ Combined    ☐ Tularemia<br>☐ Anne Arundel ☐ Anthrax<br>☐ Arlington    ☐ Smallpox<br>☐ Baltimore    ☐ Plague<br>☐ Baltimore City ☐ Botulism<br>☐ Carroll<br>☐ Charles<br>☐ Fairfax<br>☐ Frederick<br>☐ Howard<br>☐ Loudoun<br>☐ Montgomery<br>☐ Prince George's<br>☐ Prince William<br>☐ Washington | Region Status ▼<br><br>Start 01 01 2001<br>End  01 31 2001<br>Month-Day-Year<br><br>Open Slide Show |

| Detailed Maps and Charts |
|---|
| ◉ Zip Code  ○ Region |
| ○ OTC-AD |
| ○ OTC-FLU |
| ○ ER |
|   ○ URI    ○ LRI |
|   ○ UGI    ○ LGI |
|   ○ FEVER  ○ NEURO |
|   ○ CNS    ○ DERM |
| ○ SYNDROMIC |
|   ○ URI    ○ LRI |
|   ○ UGI    ○ LGI |
|   ○ FEVER  ○ NEURO |
|   ○ CNS    ○ DERM |

*Site Last Modified:*
*01/31/2001*
*For project info contact;*
*J.S. Lombardo*
*For website problems contact*
*W.A. Loschen*

Check All
Clear All
Get Detector Output

FIG. 14

METHOD AND SYSTEM FOR BIO-SURVEILLANCE DETECTION AND ALERTING

CROSS REFERENCE TO RELATED APPLICATION

This application is the National Stage of International Application No. PCT/US01/09244, filed 23 Mar. 2001, which claims priority to U.S. Provisional Application 60/191,563 filed Mar. 23, 2000, and U.S. Provisional Application 60/191,576 filed Mar. 23, 2000.

STATEMENT OF GOVERNMENT INTEREST

This invention was made with government support under contract MDA972-96-D-0002 awarded by the Defense Advanced Researched Projects Agency. The government has certain rights in the invention.

BACKGROUND OF THE INVENTION

Recent history demonstrates that weapons of mass destruction can be built and deployed by almost any individual or group that has an intent to cause harm or that is looking for media attention for its cause. The arsenal of weapons available to the terrorist includes chemical and biological agents. These weapons, banned from wartime usage, have nevertheless proliferated in third world countries. Information on the development and deployment of these weapons has become widely available on the Internet. Materials to produce some agents are also readily available. Certain biological agents pose a particularly insidious threat in that a clandestine release into a population may not be noticed during the incubation period of the resultant disease. Yet, concerning agents such as anthrax, once the symptoms are manifested it is no longer possible to treat the victim and high mortality is inevitable. Contagious agents like smallpox or the plague pose even greater threats. Such agents require early identification of an infected population in order to treat the victims and contain a potentially devastating epidemic.

Use of biological weapons therefore poses very serious crisis and consequence management issues. Various State and local emergency management plans utilize fire, rescue, and law enforcement first responders to provide emergency assistance, to control an incident site, and to collect evidence for criminal prosecution. For clandestine bio-agent releases, the medical community may be the first to see patients present with uncommon diseases. These diseases include small pox, plague, tularemia, anthrax, etc., and have a high mortality rate. In order to institute measures to contain disease outbreaks, public health officials must receive timely reports from agencies and health providers in their jurisdiction. Early warning is a key to managing an epidemic and saving lives. However, the first indicators of a bio-terrorist event may be the onset of disease in humans and animals. And professionals from the health care community may not be able to recognize the early signs of diseases that would result from bio-terrorism. Early diagnosis of such diseases is often difficult because the diseases generate only common "flu-like" initial symptoms. For example, FIG. 1 lists several characteristics of some of the most threatening biological agents, including initial symptoms associated with exposure.

To overcome the obstacles concerning an effective early warning system, improved technology is needed. Information technology and advanced telecommunications can play a major role in improving surveillance for biological weapons of mass destruction. Information integrated from multiple sources that interface with the health care needs of a community can provide early warning for the onset of an outbreak resulting from terrorist activities. FIGS. 2A and 2B illustrate the potential impact of earlier warning on the survivability of a hypothetical bio-terrorist attack. As shown in FIG. 2B, even seemingly small advances in early warning timing could save a tremendous number of lives.

However, there are significant limitations with previous attempts at constructing early warning bio-surveillance systems. Conventional bio-surveillance focuses on categorical data collected from emergency rooms, clinics, and other healthcare facilities. The detection algorithms in these conventional systems rely on threshold crossing algorithms applied to single streams of data. Such an approach does not make optimal use of available information and cannot detect a bio-terrorist attack until sizeable numbers of infected individuals appear at healthcare facilities.

Further, conventional bio-surveillance is labor-intensive. For an early warning system to be a viable option several processes must be instituted. First, data from multiple agencies that interface with human health, animal health, and agriculture must be collected and forwarded to a central integration facility. In most systems, a human analyst is needed to review all the data received to extract indicators of a bio-terrorist event. If indicators are found, the analyst needs to assemble the knowledge to form an argument. When an argument is sufficiently mature, the analyst must originate alerts to the specific organizations that need to respond to the incident. This form of bio-surveillance requires continuous support, delays alerts and may be cost prohibitive for the agencies both supporting and analyzing the data.

A need exists therefore for an automated early warning bio-surveillance detection and alerting system. Such a system should be capable of operating continuously with minimal human intervention, and should exploit the data collection and analysis capabilities of modem information technology and advanced telecommunications.

SUMMARY OF THE INVENTION

The present invention, among other things, presents a solution to the aforementioned problems associated with the prior art.

An object of the invention is early detection of health events, such as bio-terrorist attacks, in populations to enable timely responses that save lives.

Another object is to monitor multiple relevant data sets to detect signals from health events in populations that are undetectable from any single data set.

A further object of the invention is to automate monitoring of relevant data sets related to the health of populations.

The present invention is therefore an automated method and system for detecting health events in populations, such as bio-terrorist attacks, that can operate continuously and with minimal human intervention. An embodiment of the invention includes a method for bio-surveillance detection and alerting that subtracts background noise from relevant data sets using a background estimation algorithm to create residual data. The method also includes modeling the effects of a hypothetical anomalous event on the relevant data sets to create replica data. The residual data is matched with the replica data using a detector to detect a real anomalous event similar to the hypothetical anomalous event. An alert is triggered if a real anomalous event similar to the hypothetical anomalous event is detected.

Additional advantages and features of the invention will become apparent from the description which follows, and may be realized by means of the instrumentalities and methods particularly pointed out in the appended claims.

BRIEF DESCRIPTION OF THE DRAWINGS

FIG. 1 is a table listing characteristics of several biological agents.

FIGS. 2A and 2B are graphs illustrating the potential impact of improved technological surveillance on the survivability of a hypothetical bio-terrorist attack.

FIGS. 5A and 5B show county sales totals for two pharmacy chains in a test region according to one example of the invention.

FIG. 14 shows screen shots illustrating various options of a navigation bar of an on-line bio-surveillance system according to one example of the invention.

DETAILED DESCRIPTION OF THE INVENTION

The present invention is based on the following propositions:

(1) The use of chemical and biological weapons poses very serious crisis and consequence-management issues.
(2) Early warning from surveillance or actionable intelligence is a key to managing a bio-terrorist epidemic and saving lives.
(3) Professionals from the health care community may not be able to recognize the early signs of disease that may result from bio-terrorism.
(4) Modern information technology can be used for data collection and analysis to provide an early alert within a surveillance system.

Figure 3:
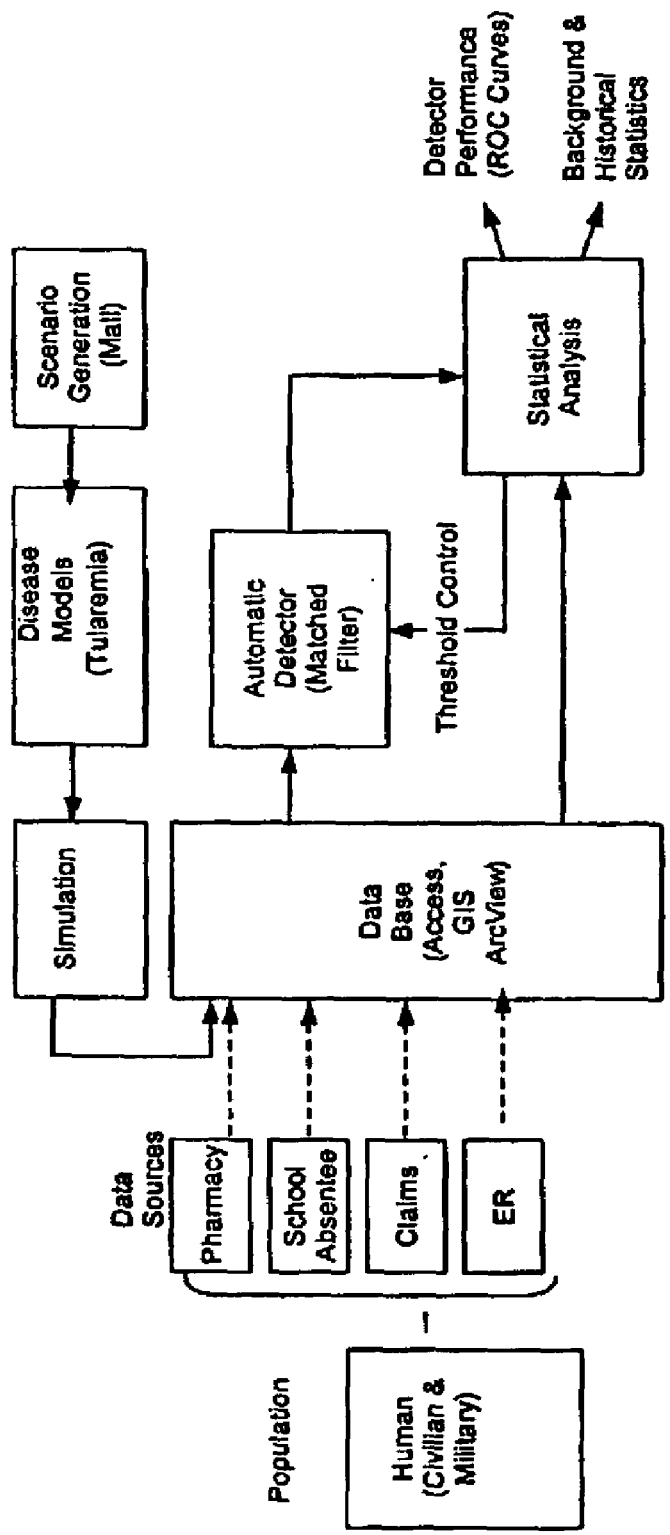
FIG. 3 is a block diagram illustrating general information flow according to one embodiment of the invention.

The present invention is therefore an automated system for detecting health events in populations, such as bio-terrorist attacks, and is designed to operate continuously and with minimal human intervention. FIG. 3 is a block diagram illustrating general information flow according to one embodiment of the invention.

Bio-warfare agents have the potential for infecting not only humans, but also plants and animals. If a bio-warfare agent sensor is at or near the site of a release, detection could occur very early. However, if such a sensor is not present the next indication of a release may be the behaviors exhibited by humans and animals during the early symptoms of disease. One behavior may be to stay home and be absent from normal daily activities, while another may be to self medicate with over-the-counter pharmaceuticals. As the disease progresses, the sick individuals may visit their family physicians who may confuse the symptoms with the latest cold or flu virus in the community. Because the physician may not be aware of other cases outside their practice, the disease could go unnoticed for several days.

Biological agents are generally delivered as aerosols. In such cases the agents will rapidly disperse until they reach concentrations insufficient to cause disease. Alternatively, they can be delivered as water-borne or food-borne agents. Regardless of the delivery method, the initial attack is an event that is local in space (relative to the size, e.g., of a county) and in time. An infected population would likely remain within a spatially local region.

The onset of disease from a bio-terrorist attack is thus characterized typically by a rapid increase in diseased individuals in a local region. A transient signal related to such a rapid increase is of such a short duration it is inevitably non-specific. Moreover, the magnitude of the transient is variable due to the uncertainty in the number of infected individuals. This implies that very simple, relatively non-specific models will likely suffice for early detection.

Practice of the present invention therefore exploits specific human behaviors exhibited during the onset of disease caused by bio-warfare agents—e.g., purchasing over-the-counter influenza medications—to provide the early alerting needed to reduce mortality. The invention involves selection of and access to relevant data sets containing information that is likely to be impacted by an event such as a bio-terrorist attack. The invention exploits non-traditional data sources like school and work absenteeism, over-the-counter pharmaceutical sales, electronically filed HMO claims as well as traditional emergency room and nursing home reports. These indicators are grouped into syndromes, weighted and correlated to obtain a view of the health status of the population at resolutions down to the zip code level.

In one example of the invention, the following data sets were used:

(1) High School Absentee Data: daily absentee and total enrollment figures from public high schools in a test county from the fall of 1997 through the spring of 2000.
(2) Over-the-Counter (OTC) Pharmaceutical Sales: sales records for the top 30 products for relief of flu symptoms, beginning in 1998, from two drugstore chains servicing the test county.
(3) Emergency Room (ER) Admissions Data: records beginning in 1998 for admissions for 470 codes related to upper respiratory illness, from a hospital in the test county.
(4) Insurance Claim Billing Records: records of ICD9 code claims related to influenza-like illness (ILI) and influenza, beginning in fall 1999, from a state agency.
(5) Nursing Home Illness Records: records of employee and resident upper respiratory illnesses beginning in December 1999 from a nursing home in the test county.
(6) Results of laboratory tests for influenza: records of influenza test results, beginning in 1998, from a state health department.

Figure 4:
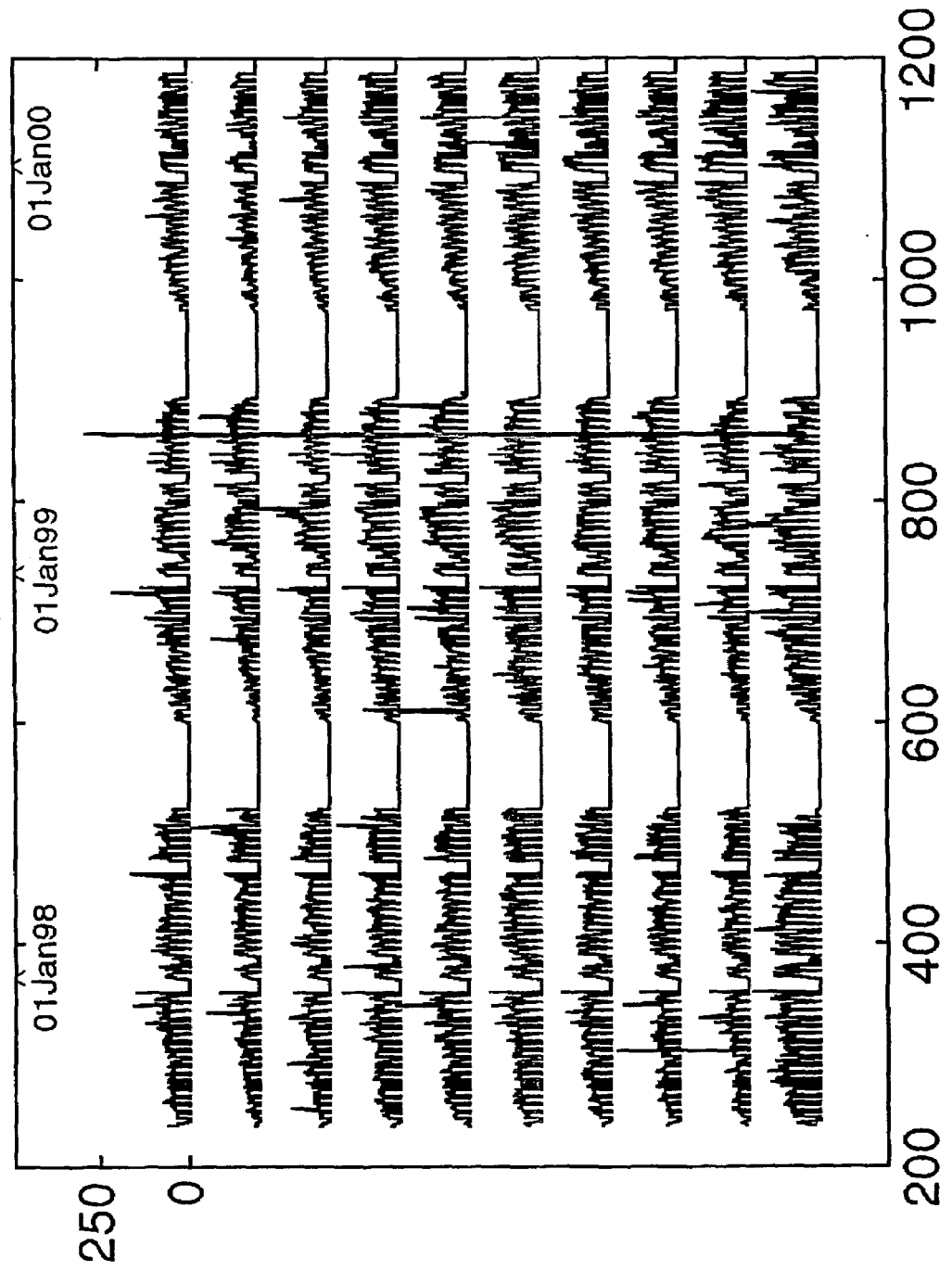
FIG. 4 is a waterfall graph showing high school absentee data used in one example of the present invention.

Samples of the data are shown in FIGS. 4 and 5. The high school absentee data were separated by school and were plotted in waterfall fashion as shown in FIG. 4. Zero absentee levels represent school vacations and weekends, and the summer vacation gaps are evident. In the search for relationships, these data were treated as dependent variables representing the effect on the population of a potential outbreak of infection. In addition to the absentee totals, weekly total enrollment figures were furnished for each school. With these totals, absentee figures for the respective schools could be expressed as rates, which allowed comparisons of absenteeism in schools of different sizes.

Figure 5B:
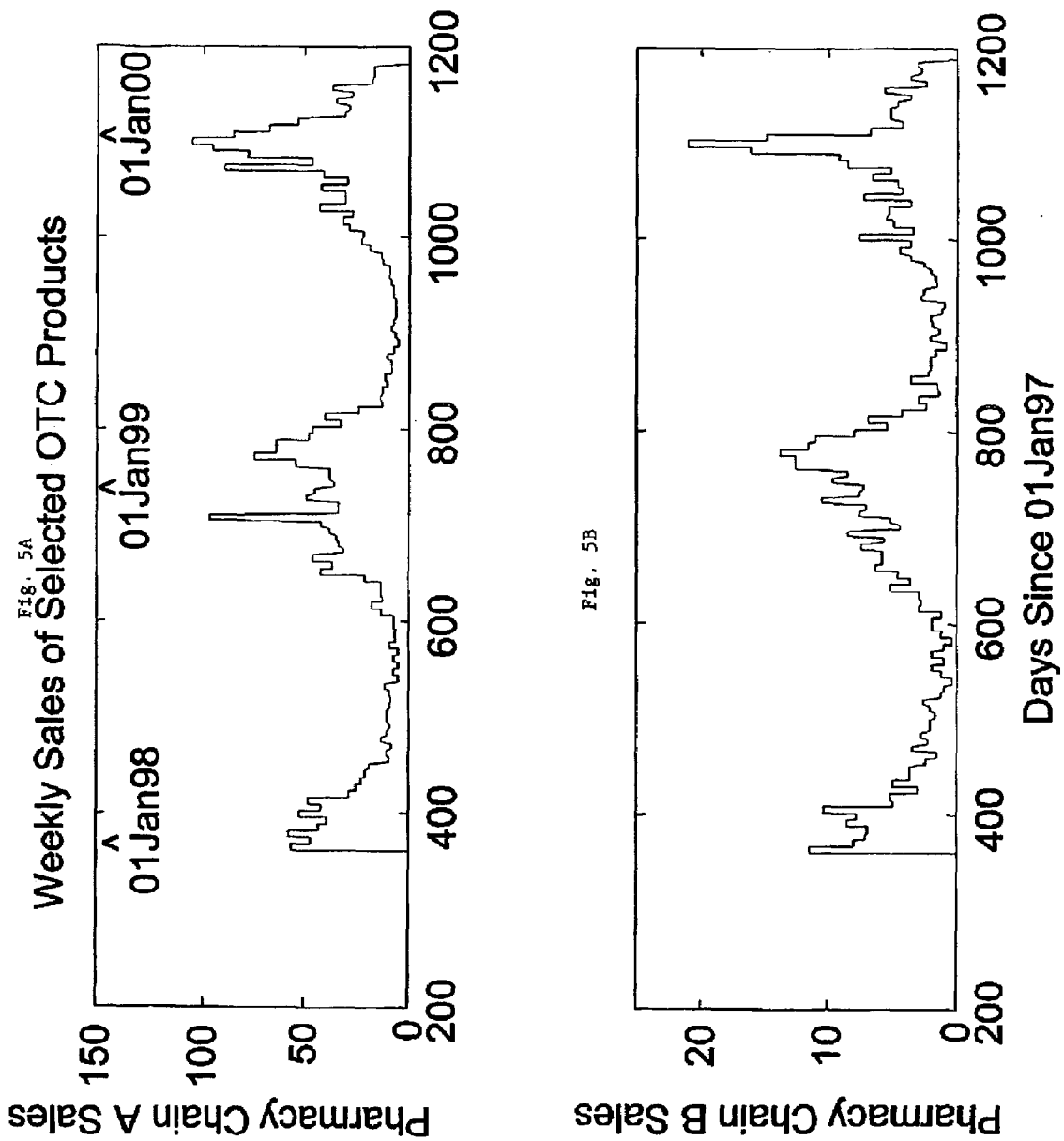

The OTC sales data give counts of the sales of a specified group of products for relief of flu symptoms. FIGS. 5A and 5B show county sales totals for two pharmacy chains in the test county. Data are plotted on a weekly scale, although daily data are available. The totals in FIG. 5A are higher than the totals in FIG. 5B because only four stores of chain B were located in the test county during 1998-2000. Influenza outbreaks of mid February 1999 and early January 2000 are evident on both plots.

A next step in the practice of the invention is to subtract background noise from relevant data sets using a background estimation algorithm to create residual data. Removal of the systematic features of the background results in a residual time series that can be described by a stationary random noise model. One then assumes that a Gaussian process describes the nonsystematic fluctuations in order to characterize the residual noise statistics by a covariance matrix that is estimated directly from the residuals.

It is an object of the present invention to detect the onset of a bio-terrorist event as early as possible; in particular, the leading edge of such an event. As described above, the onset of such an event is reasonably assumed to be characterized by the appearance of transient flu-like symptoms in the population. Moreover, the initial transient is assumed to be geographically constrained relative to some spatial domain. With an onset event that is local in time (a transient) and local in space (confined to a spatial neighborhood), relatively small anomalous events can be isolated from the large and highly systematic fluctuations that characterize the day-to-day behavior of the various data sources.

Extremely sensitive architectures for detecting spatial-temporal transients that are buried in highly complex and systematic noise are well known in nature. Retinas, for example, are an important class of such detectors. A retina consists of a membrane of cells that function as light transducers and filters. The output of a retina is not simply a function of the intensity of the visual image falling on it. Instead, the retina acts as a spatial-temporal bandpass filter. Slow, global changes in intensity are filtered out. Retinas are sensitive only to transient changes that occur over small spatial scales in the visual field.

Accordingly, an embodiment of the invention implements an algorithm that is analogous to a retina, and results in a detector that is sensitive to the onset transient of a localized bio-terrorist event. Practice of the invention may apply retinal-like algorithms over multiple spatial scales (e.g., county and statewide scales). It may also apply retinal-like algorithms to different classes of data sources (e.g., school absentee records or OTC sales data).

The above retinal-like algorithm is denoted as a center-surround algorithm. In the simplest realization of such an algorithm, each data stream is filtered by subtracting from it an amount proportional to the spatial average of the neighboring data streams of the same class.

Figure 6:
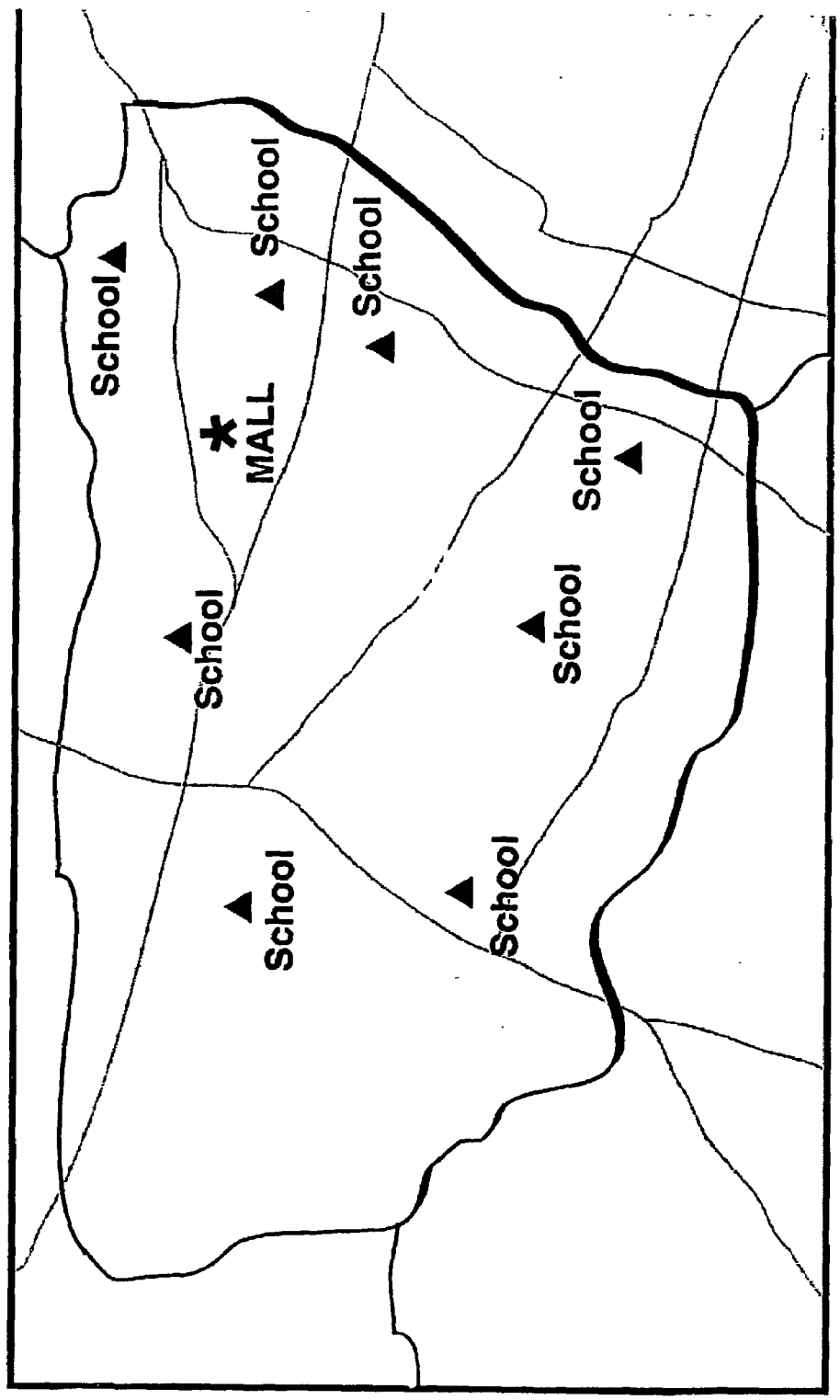
FIG. 6 is a map showing the relative locations of high schools in a test county according to one example of the invention.
Figure 7:
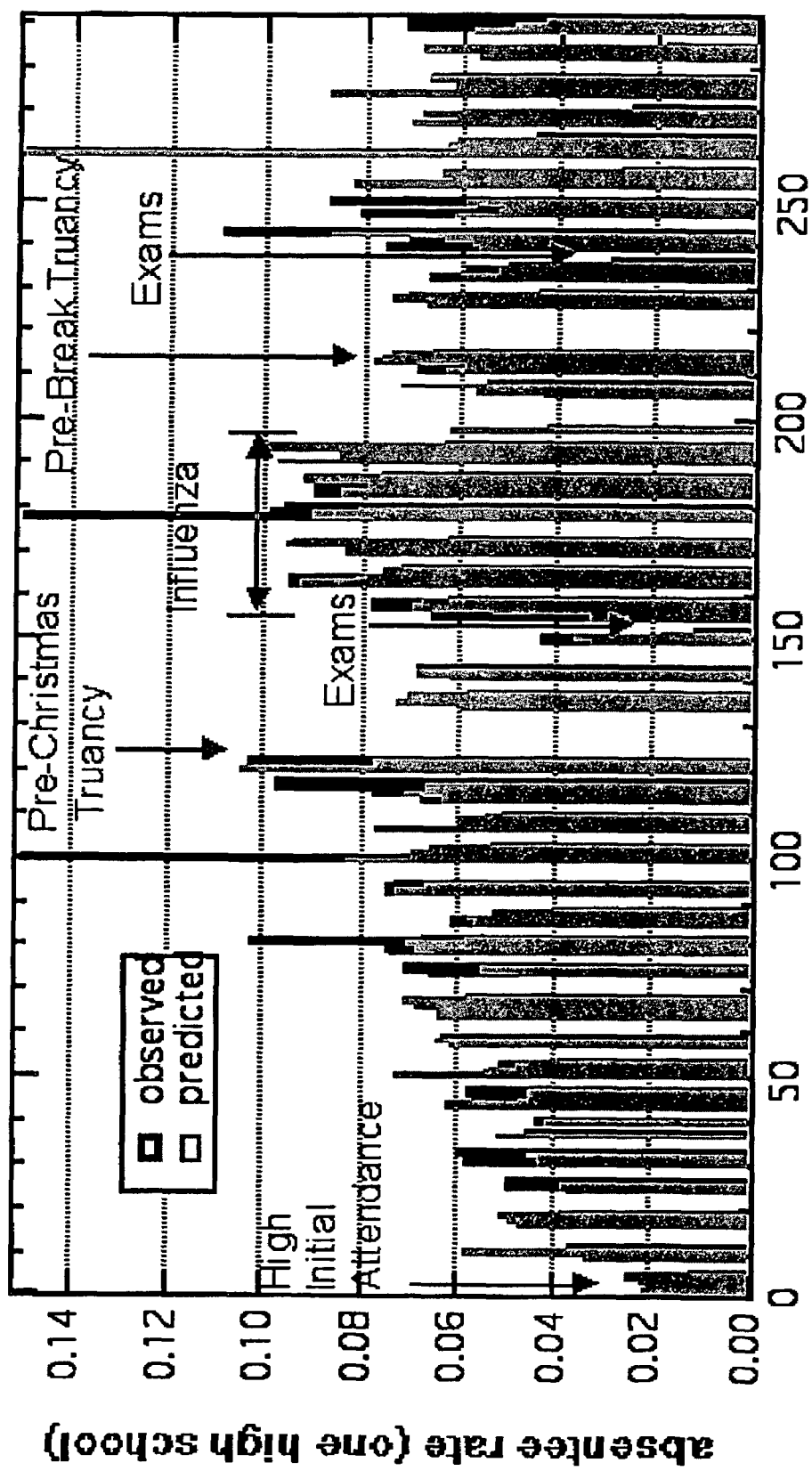
FIG. 7 is a graph showing predicted and observed absentee rates at a single high school according to one example of the invention.

The data streams included in the average are constrained to come from the data sources that are in the neighborhood of a given data source. Thus, each data source defines a "center," and its neighbors define the corresponding "surround." For example, referring to the map shown in FIG. 6, one could calculate the residuals for one school by subtracting from its data stream an average data stream computed from its neighboring schools. FIG. 7 shows a comparison of predicted and observed absentee rates at a single high school.

In the case of pharmacy data, an alternative to the background subtraction technique is to compute the average from statewide OTC sales and use the average as a reference. This procedure is justified by the empirical observation that sales from individual stores are well predicted by the statewide average just as school absentee rates in individual high schools are well predicted by the mean absentee rate of the neighboring schools (after correction for total enrollment).

A more refined retinal model is obtained by using a weighted average instead of a simple average. In the case of school absentee data, this approach is particularly effective. Empirically, it is best to estimate the background absentee rates from 6 to 12 months of historical data preceding the time frame of interest. More generally, one could consider more sophisticated models for background prediction, e.g., ARMA or TDNN models. These more refined methods can account for systematic socioeconomic effects that are manifested over time and/or space.

Center-surround techniques can be applied simultaneously over multiple time scales. In particular, depending on the resolution of the data, they can be applied at the neighborhood, district, county, state, or national levels.

The center-surround approach can be illustrated using the daily absentee rates of a set of neighboring schools as the spatially distributed sensors. Let N be the number of schools reporting daily absenteeism in a region of interest (i.e., the test county in this case). The absentee rate at school $i$, i=1, ..., J, on day t is represented by $f_i(t)$, the number of absentees divided by the total school enrollment. Our estimate of the absentee rate at school i is then:

$$f_i(t) = \sum_{j \neq i} c_j f_j(t) \quad (1)$$

The $c_j$ are adaptive coefficients fitted to a window of historical data. (Note that a precise notation would add a subscript denoting the school being modeled, i.e., the coefficients used to estimate the absentee rate for school i are more correctly written as $c_{i,1}, \ldots, c_{i,J}$. The additional subscript in the $c_j$ and in the vector c and matrix F is omitted below for simplicity.) For a chosen set of days t=1, ..., T, a separate set of these coefficients is computed for each school i by minimizing the sum $E_i$ of residuals:

$$E_i = \sum_{t=1}^{T} \{f_i(t) - \bar{f}_i(t)\}^2 \quad (2)$$

Given school i and the time window, finding these coefficients is a special case of a standard multiple linear regression problem. In this special case, the independent variable is the own-school absentee rate, the dependent variables are the other or "surround" school absentee rates, and the constant term is zero. Let f be the vector of the absentee rates $f_i(t)$, t=1, ... T, or school i, and let F be the (J-1)-by-T matrix whose (j,t) element is the absentee rate of school j on day t, skipping the chosen school i. Let c= $(c_1, \ldots, c_{J-1})$ be the vector of coefficients of the surround schools. Then, by the standard method of differentiating with respect to each $c_k$ and setting the resulting expressions equal to zero, the coefficients are given by:

$$C = (f*F^T)*(F*F^T)^{-1} \quad (3)$$

Note that for each chosen time window, these coefficients must be computed for each school. The linear algebra for this operation is straightforward and well known.

Referring again to FIG. 7, it shows a comparison of observed school absentee rates at a typical high school during the 1998-99 school year versus the rates predicted using those of neighboring schools. As expected, some of the systematic features of the actual rates are reflected in the predictions; the low truancy at the beginning of the year and the drop in attendance before school vacations match reasonably the estimated absenteeism. School-specific causes of absenteeism—or a localized outbreak of infection—will not match the predictions.

Using a Kalman filter is an alternative to the above-described background subtraction techniques. A Kalman filter requires the specification of a number of state variables. In the present invention, the state variables would represent the fundamental health state of a population. For example, the number of people with various natural diseases and also the potential number of people with initial disease caused by a terrorist event. Next, a Kalman filter incorporates known input variables such as the day of the week, season of the year, dates of holidays, price-reduction sales events, weather, etc. From the state and input variables, models describe the predicted effect of an event on the measured data streams. In the present invention the models would be stochastic in nature. A Kalman filter optimally estimates the state to minimize the difference between the prediction and the current measurements. The efficacy of a Kalman filter depends on the ability to develop accurate models for the effects influencing the indicator data streams.

A next step in the practice of the invention models the effects of a hypothetical anomalous event, such as a bio-terrorist attack, on the relevant data sets to create replica data. Replica data is defined as data that simulates the effects of a health event on a relevant data set that is monitored by the methods of the present invention. The replica data may be based, for example, on input from epidemiologists and various scenario templates including information on disease manifestation, pathogen release models, dosage estimation, and other intelligence. Models also may exploit historical data from, for example, influenza epidemics.

One way to perform this step is to use adaptive matched filters. The adaptive matched filter was developed in the radar community as an optimal detector in the presence of Gaussian noise and has been used widely in a variety of noise environments. This technique is appropriate for problems in which time variation of the signal is known sufficiently to model the signal as a mathematical replica. The matched filter is designed to find signals that match the expected replica signal and to reject signals or noise that are unlike the replica. The usual procedure effectively takes the normalized inner product of successive segments of an input data stream with the replica to obtain successive products. Thresholds are then applied to these successive products to make detection decisions.

An adaptive matched-filter approach is useful for a bio-surveillance detector for two main reasons. First, the ramping and peaking of public health data sources at the onset of an infection outbreak indicate a time-varying signal, and this time variation may be quantified using models for the outbreak behavior. Such models must be based on known characteristics of the infection, on estimates of the populations involved, and on how behaviors of those populations are exhibited in the public health data being observed, which can be determined from observed population behavior during influenza season. Unlike radar or sonar, the data vary on a time scale of days instead of fractions of seconds.

A second advantage of an adaptive matched filter is its ability to handle disparate noise characteristics from different data sources. An optimal detector must consider the noise background as well as the signal model. It should suppress data streams that have significant noise fluctuations that may imitate the desired signal and cause false alarms. However, data channels with low noise should be emphasized for increased detector sensitivity. In combining data from multiple sources, the adaptive matched filter makes an optimal tradeoff between signal and noise in each data source. The adaptive matched filter estimates the noise in each channel with covariance matrices computed from data residuals. The residuals are obtained from the data by subtracting adaptive background values. Methods of estimating the background depend on the type of data being processed.

For an implementation of the matched filter, suppose that the filter extends over N days of data and that $X_i$ is the vector of residual data at day i. Typically, the first J elements of $X_i$ are residuals derived from absentee rates of schools 1, ..., J for that day, the next K elements are from OTC sales at stores 1, ..., K, etc. Let $C_i$ be the estimated covariance matrix of $X_i$, and let r be a replica vector of modeled effects of the outbreak on the data. The normalized replica is then $M_i = r^T/(r\ C_i r)^{1/2}$, and the adaptive matched-filter statistic is:

$$y = \sum_{i=1}^{N} M_i^T C^{-1} X_i \qquad (4)$$

The replica normalization is done to ensure that y has standard deviation σ=1, so that computed values of this statistic may be readily compared to thresholds at multiples of a standard deviation.

Following is a specific example of the use of a matched filter involving disparate data streams. The matched-filter detector was subjected to a plausible test for a preliminary evaluation of the approach. The input data required for this test were the simulated effects on the available data sources of an outbreak of infection triggered by the airborne release of a toxic agent in a crowded public area.

The hypothetical threat chosen for the data simulation was the infectious disease tularemia. This disease is caused by the bacterium *Francisella tularensis*, found worldwide in wild animals, birds, and insects. Humans contract tularemia most frequently by physical contact with animals carrying the organism or from tick bites, but the less common pneumonic form of the disease may be contracted by inhalation. Tularemia was weaponized by the former Soviet Union, hence its choice here as a hypothetical airborne threat. After a 3- to 5-day incubation period, victims become acutely ill, with a 5 to 15% mortality rate. Treatment with antibiotics lowers this rate to about 1%; thus, a detector that could speed the alerting of public health personnel could save lives.

A shopping mall in the test county mentioned above was chosen as the site of the hypothetical bio-terrorist event. Demographic data were obtained from the mall management to allow estimates of the size and likely age distribution of the exposed population. These estimates were combined with plausible infection rates and with the knowledge of the effects of widespread upper respiratory illness, seen during influenza outbreaks, to model the effects of an outbreak of pneumonic tularemia on the data sources.

The demonstration used four disparate data sources: OTC sales from pharmacy chain A, insurance claims, nursing home illnesses for both residents and employees, and ER admissions. For each case, countywide daily totals were used to the extent that they were available.

For the successful application of adaptive matched-filter theory, the data streams must exhibit stationary noise. However, the raw data channels used in the demonstration exhibited significant non-stationary activity in response to such events as weekends and holidays, snowstorms, and price-reduction sales. These non-stationary events can be successfully removed by exploiting their spatial behavior. In cases where significant numbers of spatial samples were available, the center-surround technique described previously could be used to remove the non-stationary events. A simpler version of spatial normalization was utilized for cases where current data were available from only one county and statewide. In these cases, the background values were estimated from data taken on a statewide scale, scaled, and subtracted from the local data streams to obtain the stationary residuals. Covariance matrices were computed by averaging the outer products of the residual vectors with themselves:

$$C = \Sigma X_i * X_i^T \qquad (5)$$

where the averaging is over a suitable time interval preceding the new data. These matrices were approximately 10-week averages; much shorter averages produced noisier matched-filter output.

An artificial signal was formed by adding to each data stream the modeled effect of a hypothetical bio-terrorist event. The magnitude of this signal, reflected in the number of additional OTC sales, insurance claims, etc., was proportional to the assumed number of people infected because of the event. Modeled infection rates ranged from 16% (~1140 infected) to 0.3% of the people exposed to the toxic agent at the mall site. A week during mid-winter was chosen for this event so that the effects of the flu season would provide authentic masking of the signal.

Figure 8B:
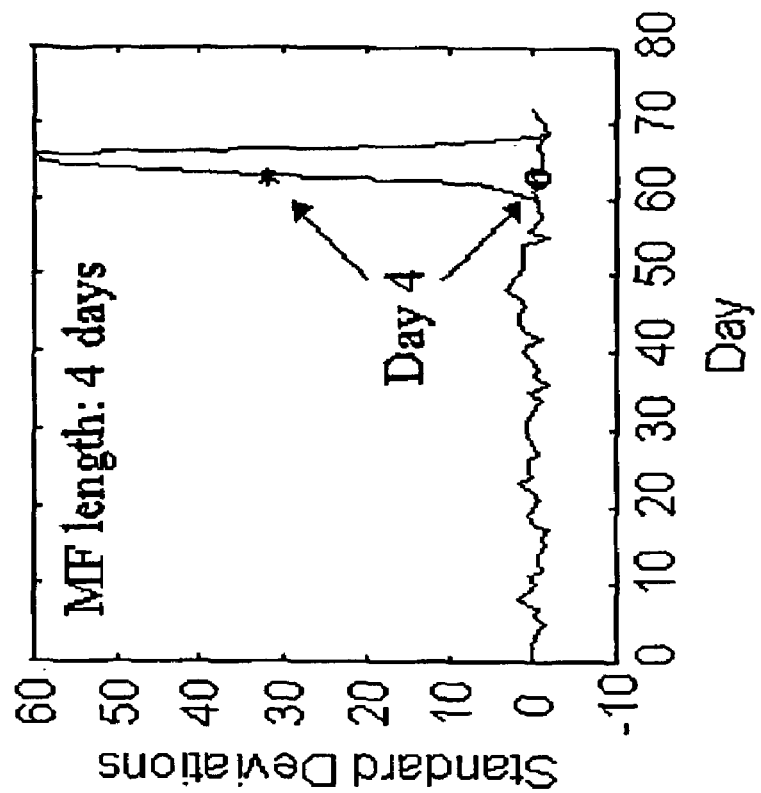
FIGS. 8A and 8B show examples of matched-filter output for filter lengths of three and four days, respectively, for a 16% infection rate, according to one example of the invention.
Figure 8A:
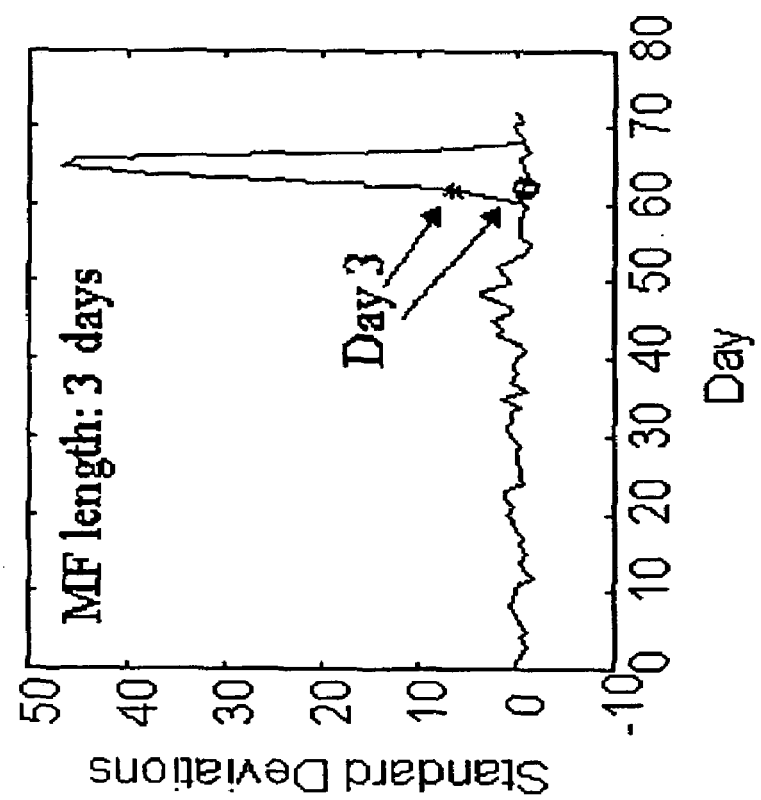

The matched-filter statistic y was computed both for unmodified data residuals and for residuals with the artificial signal added to simulate an infection outbreak. FIGS. 8A and 8B show examples of matched-filter output for filter lengths of three and four days, respectively, for a 16% infection rate. In both figures, the "*" and "o" symbols indicate matched-filter output with and without, respectively, the added signal on the third day after incubation of the released agent, a couple of days before measures would otherwise be taken to deal with the outbreak. The difference in normalized units is six standard deviations on the day in question, while the output without the signal never rises above four standard deviations for the 72-day period shown; thus the matched-filter output appears to be a reliable early alert. By the fourth day, as shown in FIG. 8B, the impact of the signal is more striking and would be seen in the output even amid a severe flu season or other noisy conditions.

Figure 9A:
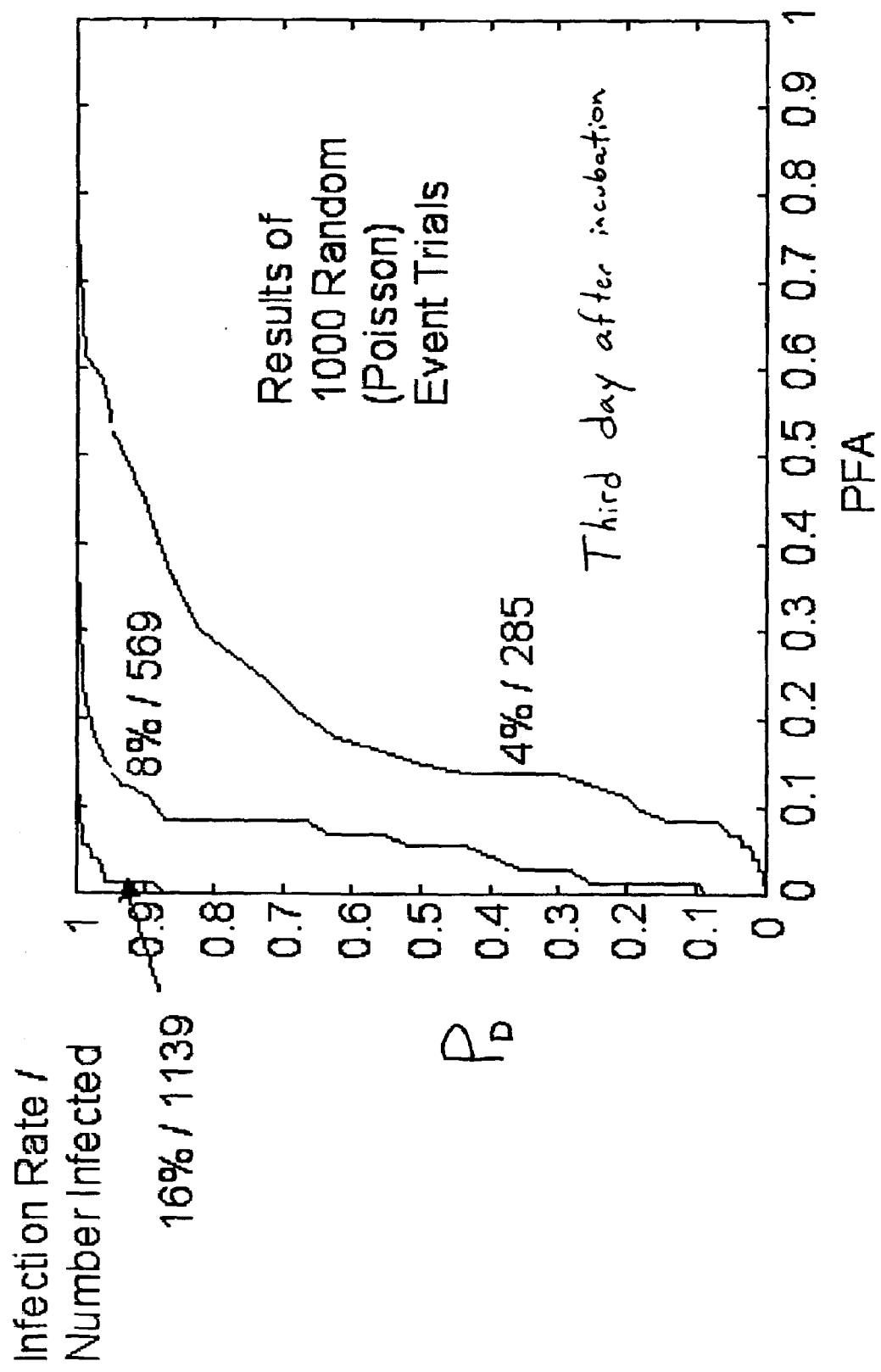
FIGS. 9A through 9C contain plots of Receiver Operating Characteristic (ROC) curves that show detector performance on the third, fourth, and seventh day after incubation, respectively, according to one example of the invention.
Figure 9B:
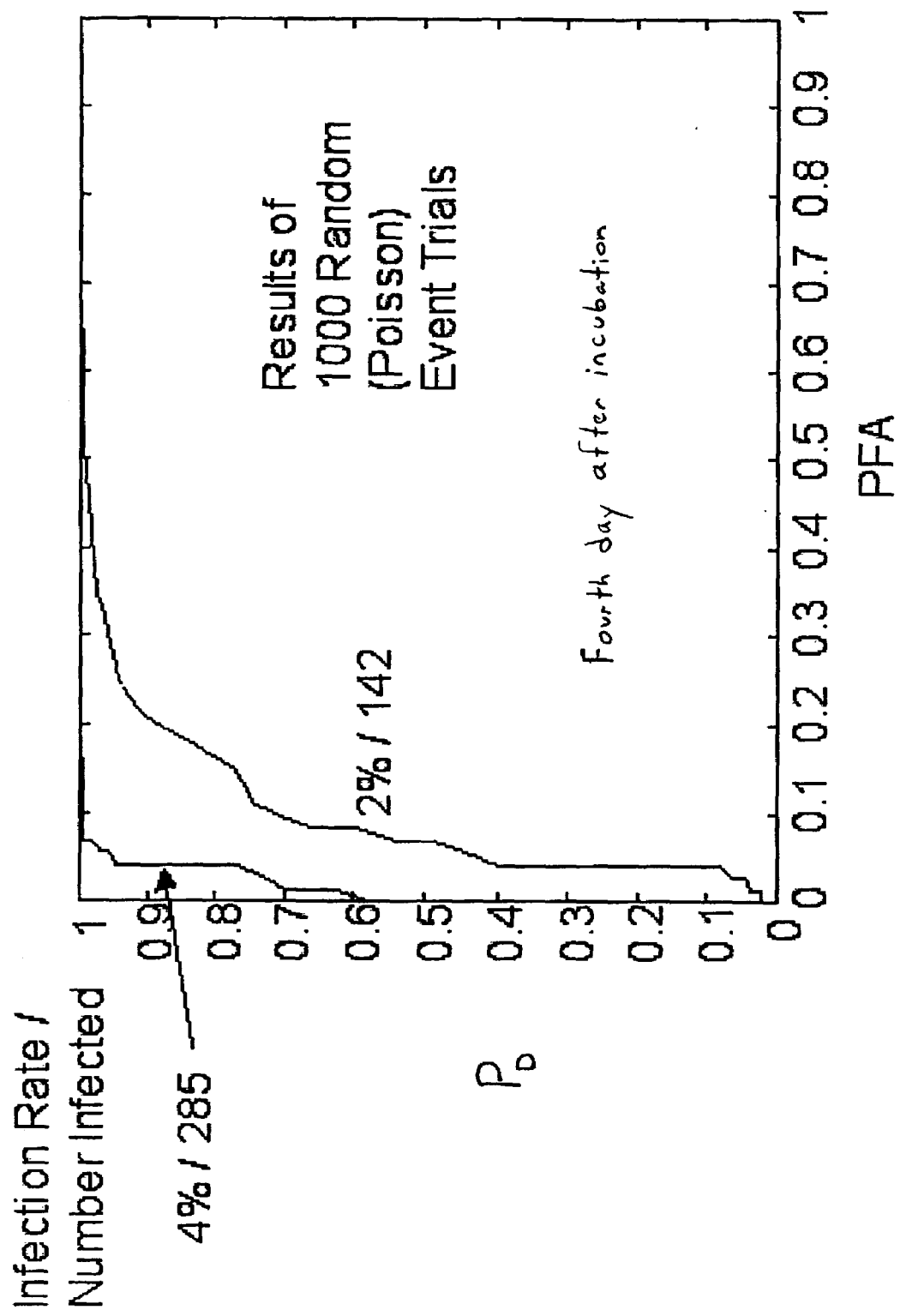
Figure 9C:
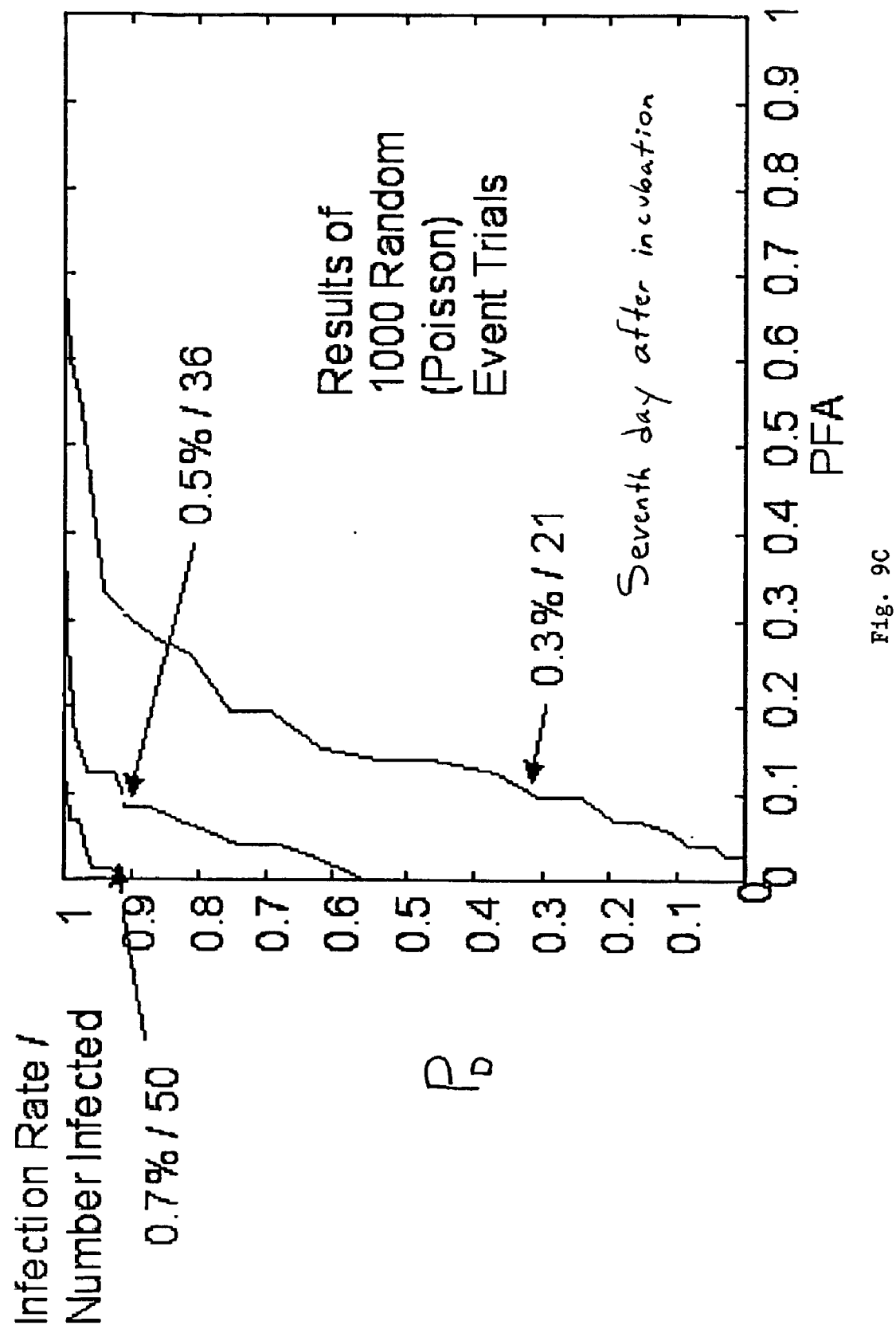

In the above example, the replica perfectly matched the simulated signal that was injected into the data. It is unlikely that one would be able to model a real anomalous event (e.g., an actual bio-terrorist attack) that precisely. To examine the robustness of the techniques with respect to variation from a perfect model, a Monte Carlo simulation was performed with 1000 random trials. In each trial, a random signal was drawn from a Poisson distribution whose mean matched the replica. Thus, there was generally some degree of mismatch between the signal and the replica. Results of the simulation are summarized by receiver operating characteristic (ROC) curves. These curves plot the detection probability and the false alarm rate as the threshold is varied. FIGS. 9A through 9C contain plots of ROC curves computed from this set of simulations and show detector performance on the third, fourth, and seventh day after incubation, respectively. Individual curves represent different infection rates as labeled and thus different signal-to-noise ratios in the data. For the larger rates and stronger signals, the detector yields high probabilities of detection ($P_D$'s) relative to probabilities of false alarm (PFA's). For example, on the fourth day, a 95% $P_D$ is achieved with a PFA of only 5% for the case of a 4% infection rate. By the seventh day, outbreaks resulting from much smaller infection rates are detected.

A second specific example is described below involving center-surround absenteeism data on a local scale.

The second example utilized the absentee data discussed above. Data streams were the daily absentee rates of ten high schools. For each school, the center-surround predictions from the other 9 schools were used as the background data estimate.

The signal-generating event was again the hypothetical toxic aerosol release at the shopping mall location. The signal was constructed to simulate the relative effects at each school according to the distance of the school from the release site. The release date was set on a Saturday in February 1999, a time when the mall demographic data show that a large number of students would have been exposed and also a time after the school Christmas break so that the absentee data could be used. In the added signal, absences due to the tularemia infection were increased for a week to represent the variable incubation period and then dropped from the absentee rates because the disease is not communicable among humans.

For each day, the number of infected students from school j was calculated as N(j), the total number of infected high school students on that day times the conditional probability:

P[S(j)_M]=probability of enrollment at school j given presence at the mall. The vector of values of N was computed from the demographic data and from the assumed infection rate. Values of P[S(j)_M] were computed using the Bayes Theorem for conditional probability. Let P[M_S(j)]=probability of presence at the mall given enrollment at school j P[M & S(j)]=joint probability that a student is at the mall and attends school j P[S(j)]=probability that a county public high school student attends school j Then, the desired probability is $$P[S(j)\_M]=P[M \& S(j)]/P(M), \quad (6)$$

where the usual inversion of conditional probability gives:

$$P[M \& S(j)]=P[M\_S(j)]*P[S(j)] \quad (7)$$

$$P(M) = \sum_k P[M \& S(k)] \quad (8)$$

and the two probabilities on the right side of Eq. (6) follow from knowledge of the vectors P[M_S(j)] and P[S(j)].

However, P[S(j)] is simply the local school enrollment divided by the total enrollment. Components of vector P[M_S(j)] were estimated according to the distance of school j from the mall, and used with Eq. (6) to compute the number of infected students in each school. The vector of these infection counts for all schools was used as the replica for the matched-filter processing. These counts were also added to the absentee data on the days chosen for the hypothetical event to add a signal to the noise.

The matched-filter implementation of Eq. (4) requires the matrix $X_i$ of residuals obtained by subtracting a background process from the signal-plus-noise data for all 10 schools on each day in question. (Thus, the matrix $X_i$ represented 10 data streams.) The background in this case was the set of center-surround absenteeism estimates from the neighboring schools, as described above. The covariance matrices C were formed and updated by averaging the outer products $(X_i*X_i^T)$ for a full school year preceding the day addressed. The availability of the complete set of absentee data for this length of time yielded stable matched-filter behavior.

Figure 10:
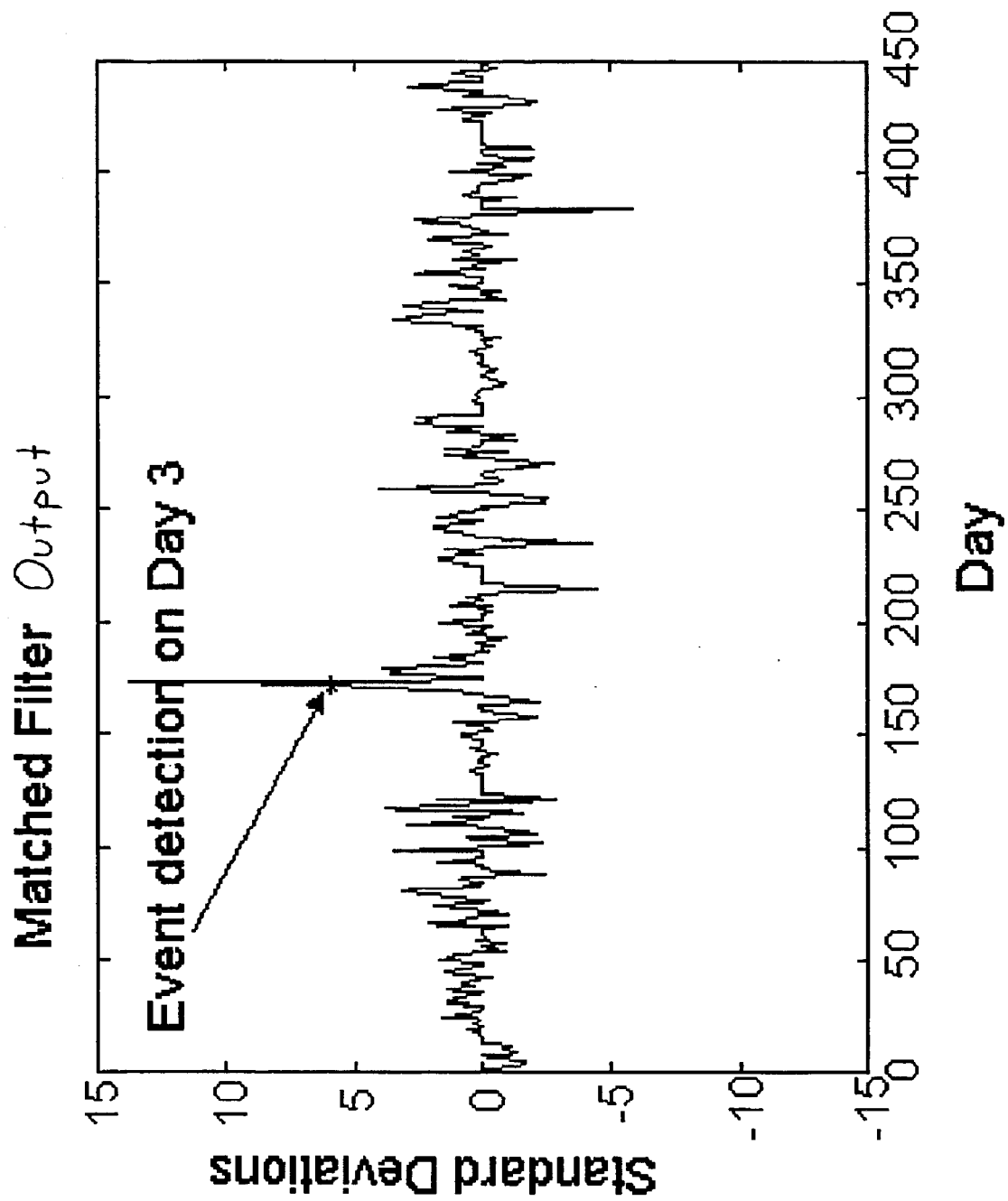
FIG. 10 is a graph showing the matched-filter output according to one example of the invention.

An infection rate of 16% was assumed for the simulation. The matched filter was run over a period of 450 days, exclusive of summer vacation. FIG. 10 shows the matched-filter output. The starred value of six standard deviations of the matched-filter statistic occurs on the third day following the modeled incubation day, again suggesting an early alert with an extremely low false alarm rate. By the fifth day, the statistic reaches a value of 12 standard deviations before it returns to the background value.

The above example demonstrates the effectiveness of an adaptive matched-filter. In conjunction with the spatial normalizing-techniques, the adaptive matched filter can produce an early detection of a simulated localized terrorist attack with a high $P_D$ and an extremely low false alarm rate in the presence of real noise data, even during an active flu season.

Below is a third example of the present invention that includes a demonstration of the detector with multiple data sources versus only Emergency Room (ER) data. For this demonstration, data sources from high school absenteeism, OTC sales, insurance claims, nursing home illness records, and emergency room visits were all included. The February 2000 mall infection event simulation described above was repeated using the requested data sets and an assumed infection rate of 16%.

The center-surround methodology was generalized and applied to those data sets for which data could be separated geographically. The OTC sales for pharmacy chain B were separated by the store of purchase, while insurance claim and ER admission records were sorted by patient zip code. For the chain B OTC sales, the four county stores were treated as center-surround neighbors so that background estimates for each store could be formulated as adaptive linear combinations of the other three. This procedure was not as straightforward for the zip code divisions because the test county zip codes comprise vastly different populations, from entire towns to neighborhoods. The insurance claims were therefore lumped by patient zip code into eight geographic regions with the aid of a county zip code map and a histogram of claims by zip code. These eight regions were treated as center-surround neighbors. A similar procedure was used to group the sparser ER admissions data into six regions. The aggregate of all of these data groups comprised 31 individual data streams.

To simulate the effects of the outbreak, two Bayesian probability vectors were estimated for each set of surround groups. First, the simple probabilities of belonging to each group were determined. For the case of absentee data, relative school enrollment data were used to calculate individual school probabilities. For the other cases, the relative population of each group was used. Second, given membership in each group, the conditional probabilities of exposure to the event at the mall site were also required. For the high schools and pharmacies, the reciprocals of the driving times to the site were used, since driving time was seen as a more realistic influence on these probabilities than physical distance. For the zip code regions, population centroids were roughly estimated, and reciprocal site driving times from these centroids were used.

With these probability estimates in place, a signal representing the effect of the toxic agent release on all 31 data streams was computed for seven days. This signal was used as the matched-filter replica and was also added to the data to simulate the bio-terrorist event. Within each center-surround group, residuals were formed for each data stream by subtracting the background estimate from the data with the signal added. The full set of residuals formed the vector $X_i$ of the matched-filter implementation of Eq. (6). For the noise-only case, these residuals were calculated without the addition of the signal.

As before, the covariance matrices were formed by averaging the outer products $(X_i* X_i^T)$; the lack of a long history for all of the data sources limited the averaging time. An averaging length of 84 days produced fairly stable matched-filter output.

Figure 11B:
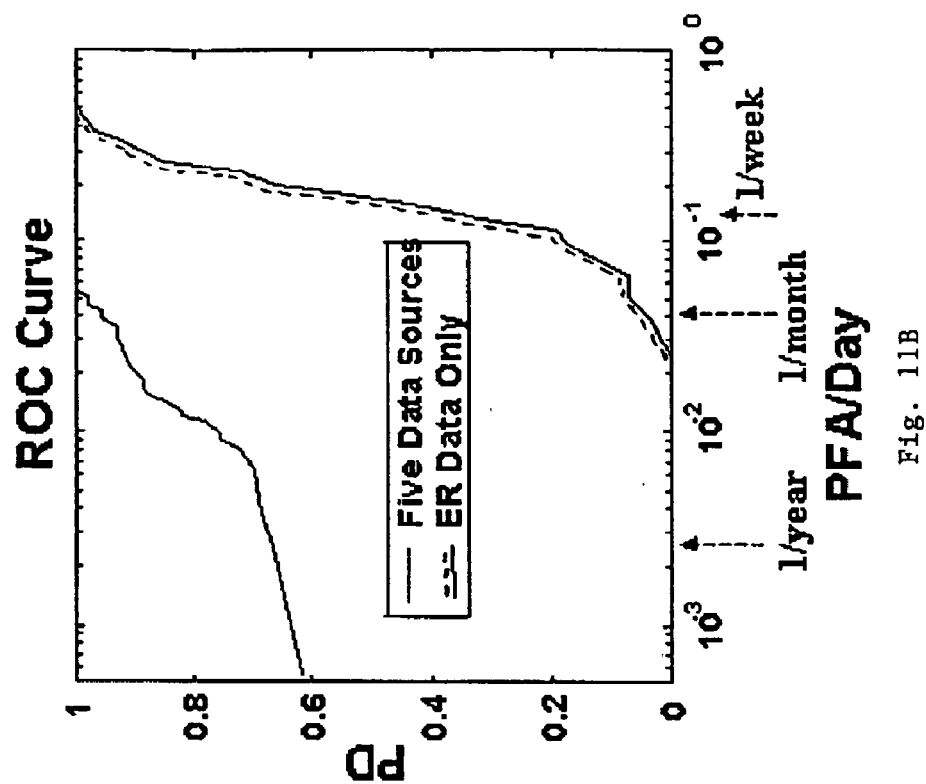
FIG. 11B is a graph showing ROC curves computed for the same two cases from the same 1000 runs depicted in FIG. 11A.
Figure 11A:
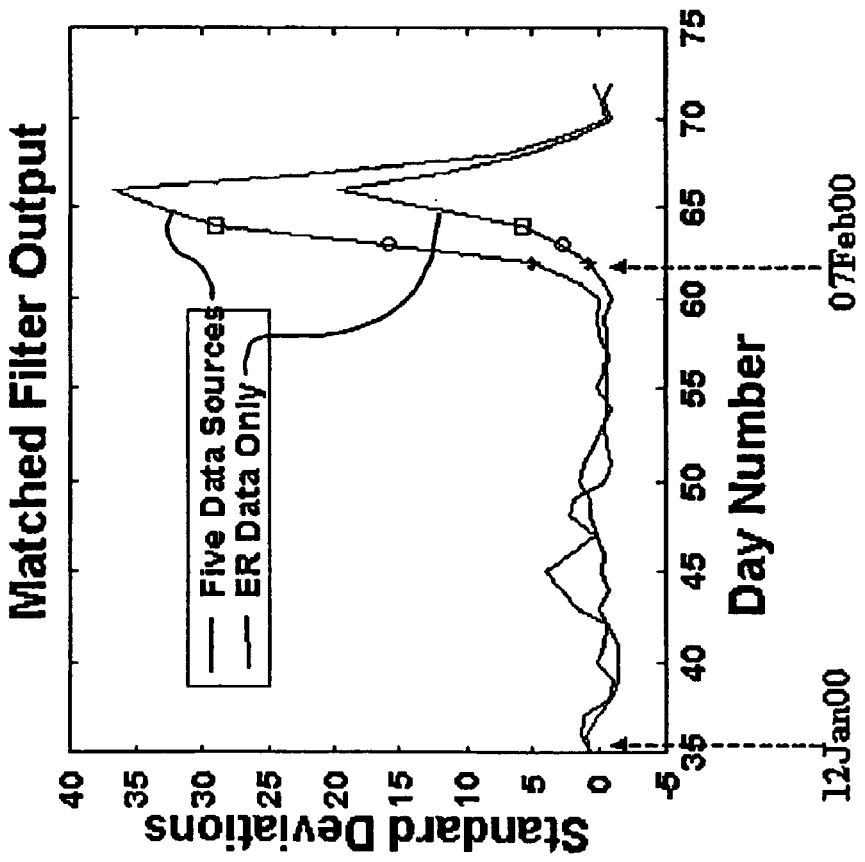
FIG. 11A is a graph showing the averaged matched-filter output curves computed using five different data types and ER data only, according to one example of the invention.

The plots in FIGS. 11A and 11B summarize the results of the comparison. FIG. 11A shows the averaged matched-filter output curves computed using all five data types and ER data only. The curves were averaged over a set of 1000 runs. An infection rate of 16% was assumed for each individual run, but the distribution of the signal among the data streams was varied each time with draws from a Poisson distribution. The plotted symbols represent the respective output levels for three consecutive days beginning Feb. 7, 2000, three days after exposure—i.e., just after the earliest incubation of the tularemia. A key observation is that the five-source output level on this date is two days ahead of the output for the filter using ER data only. In other words, this example demonstrates a potentially life-saving advantage of two days of alert time if all of the data sources are used.

FIG. 11B shows ROC curves computed for the two cases from the same 1000 runs. From the standpoint of ROC analysis, the advantage of using the extra sources is considerable. The horizontal axis gives false alarm probabilities, with arrows indicating the probability of a single false alarm per week, per month, and per year. At a level of one false alarm per month, the $P_D$ for the five-source case is about 95%, but it falls below 10% if only ER data are used.

Figure 12:
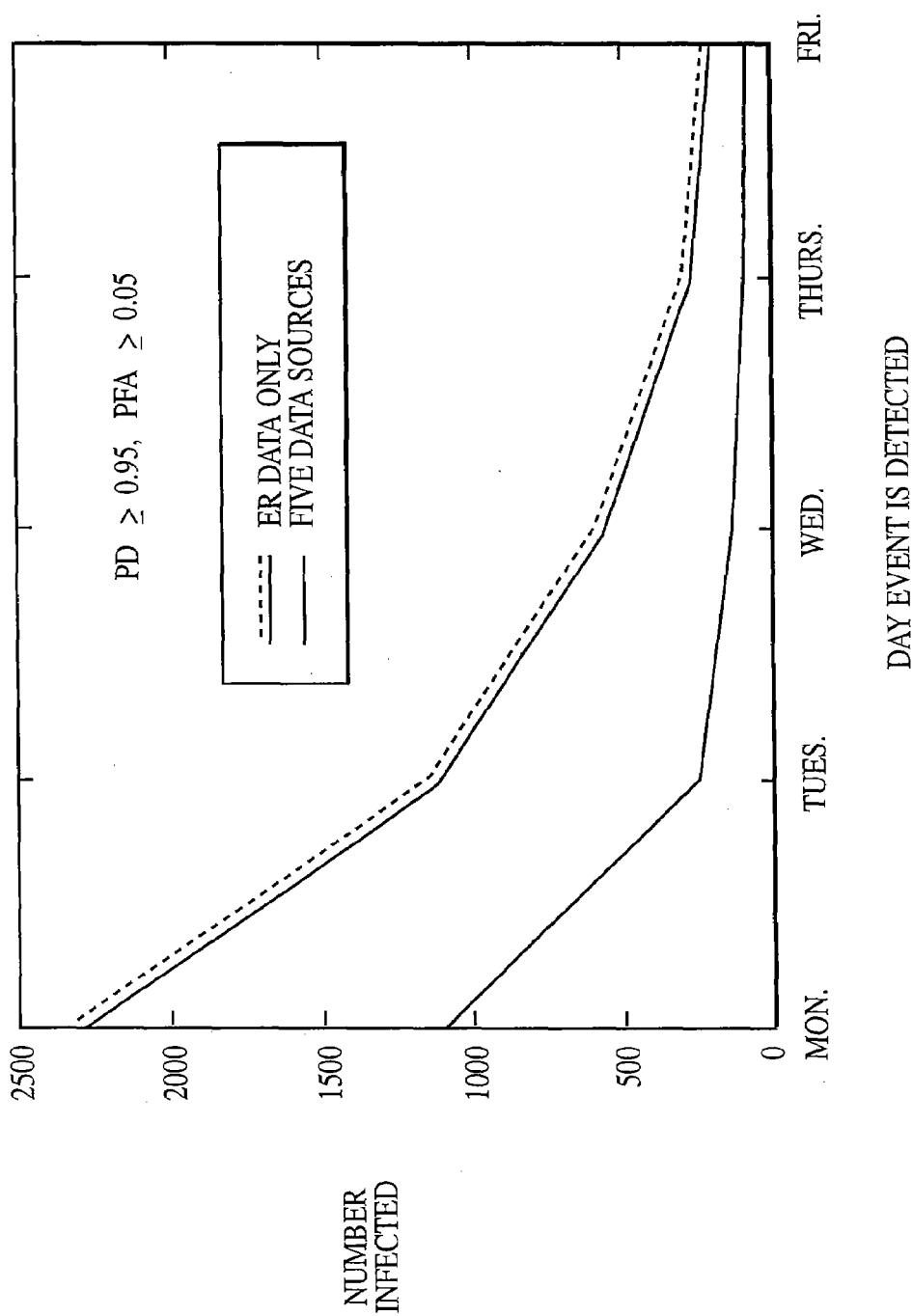
FIG. 12 is a graph showing the number of victims required for $P_D \geq 0.95$ with $PFA \leq 0.05$ as a function of days after the earliest incubation of a disease according to two examples of the invention that use different data sources.

For a final comparison, the set of 1000 trials was repeated for each of a set of lower infection rates ranging from 8% to 0.3%. The purpose of these runs was to determine how small an outbreak—i.e., how weak a signal-could be detected. FIG. 12 summarizes the results obtained by plotting the number of victims required for $P_D \geq 0.95$ with $PFA \leq 0.05$ as a function of days after the earliest incubation of the disease. The number of victims was obtained from the ROC curve for each infection rate that satisfied the probability requirements. The summary is shown for the detector using the same two sets of data: the solid curve represents the full set of data sources with all 31 data streams, while the dashed curve represents only ER data. According to this comparison, for the crucial days following the earliest incubation of the disease, the number of victims required for an alert when all five data sources are used is half of that resulting from the use of ER data only.

In summary, the above examples illustrate a single detector in a fixed data environment. Data streams were used from actual records of emergency room visits, over-the-counter drug sales, school absenteeism, insurance claims, and nursing home illnesses. The examples demonstrate that the techniques of the present invention enable early recognition of an infection outbreak by processing small, nearly synchronized increases in several disparate data sources before the outbreak would become obvious in any one of them. A matched-filter detector was devised to enable the early alert desired. This detector was exercised by simulation of the data effects of widespread infections caused by the hypothetical release of a toxic biological agent in a public area. Current demographic data and the expertise of an epidemiologist were used to estimate the effects on the various data streams and to create the replica data. In the simulated scenarios, the detector results were clear enough to permit notification of public health authorities two to three days before a likely conventional alert based on emergency room admissions.

Other embodiments of the detector of the present invention include the use of Neyman-Pearson detectors, change detectors and Bayesian Inference Networks. General Neyman-Pearson detectors could be used to improve receiver-operator-characteristics. This includes the use of nonlinear filters, e.g., neural-network-based density-estimation of non-Gaussian statistic filters.

Change detectors, as used with the present invention, are based on the theory that data are drawn from a random distribution. Then at some point in time the distribution changes. Detection of the time of the change is accomplished through various combinations of samples of a log-likelihood ratio. There are similarities between the use of a change detector and an adaptive matched filter. However a primary difference is the fact that a change detector is designed to minimize the time delay between the time of change and its detection; while an adaptive matched filter is designed to maximize the signal-to-noise ratio. Change detectors take the general form of an integrator applied to a series of log-likelihood ratio samples. The integration is useful in reducing the background noise variance, so that the detector does not trigger on every noise fluctuation. One implementation of change detection theory is the application of an integrator to the output of a matched filter. The duration of the integrator must be carefully chosen to ensure short duration events are not missed. Nevertheless, integration over just a few samples (e.g., days) of data could produce a significant integration gain.

Finally, Bayesian Inference Networks could be employed as detectors. Bayesian networks have been shown to be an efficient and general way of representing complex distribution functions incorporating both discrete and continuous variables.

Still another embodiment of the present invention includes an automated expert that can maintain the effectiveness of the detector as a function of changing demographics, consumer behavior, and other input data characteristics. This maintenance function may be served by a test/evaluation capability for the automated agent, including the generation, execution, and analysis of a set of benchmark scenarios, and by a capability to modify the detectors.

Yet another embodiment of the invention includes a methodology to draw inferences from detections, such as the location and scale of a suspected outbreak, the portion of the population at most risk, the type of agent responsible, etc. Such features further enhance the alerting capability of the invention.

Specific Example of an On-Line Bio-Surveillance System

Following is a detailed description of an internet-based embodiment of the present invention that incorporates the background subtraction and detection algorithms described above. The present embodiment (referred to here as the "On-Line Bio-surveillance System") is a graphical web-based system that allows users to plot many data sources in many combinations onto a single map. It gives users tools to manipulate data and is both an alarm based and information based system. It has features to help those in need of seeing alerts and potential disease hot spots, as well as those who just need to see the details of incoming data.

The On-Line Bio-surveillance System described in detail below is an example of one embodiment of the present invention that is a graphical web-based system that allows users to view Geographic Information System (GIS) based images of bio-surveillance data. The data are processed according to the techniques described above and are plotted across the National Capital Area, which includes parts of Maryland, Virginia, and Washington, D.C. Practical uses of the system include alerting users of a biological attack, as well as providing general health information to epidemiologists and local health officials. The data that an individual on-line user is authorized to view are a function of the access level of the user. For example, county public health officials would only be able to access data for their county, while state public health officials would have access to statewide data.

The system is completely controlled by the user. ESRI ArcView® GIS is the map-generating component of the system and Microsoft Access® is the database for the system. The system connects ArcView®, Access®, and the user via a web browser and employs static pictures in its displays. It should be noted that the system was built using ArcView® and Access® but that it is not limited to these applications. Any software that provides the basic features of these applications can be used.

Due to data size constraints, and the nature of putting information on the internet, a system designer should ensure that on-line images are both useful and give the most information per pixel as possible but without giving too much information to the user. This may be accomplished by several methods. A first method is to generalize some of the data sources from specific named sources to more general terms. A second method is to display the data normalized against itself, and then display the levels, instead of the actual numbers. Not only does the latter method solve privacy problems associated with putting specific numbers on a website from which users may gather more information than intended, but it also can result in a more valuable representation of data. The technique of normalizing is done using running averages and standard deviations. For each category, a running average is stored. A running standard deviation is also stored. After subtracting the average from a current value, one divides that result by the standard deviation to determine the number of standard deviations away from the average. By normalizing the data against itself in this way, one can then display the level of the data instead of the original values. This technique provides a common alerting threshold across all data. With just one color-scheme and one legend, every type of data can be displayed on the same scale. This also facilitates the comparing of multiple data sources.

Another issue includes operations and maintenance of the system. When dealing with a high volume of data and images, the process of dealing with the everyday tasks of maintaining a system must be as automated as possible. One method for accomplishing this uses, for example, Avenue scripts for the ArcView® tasks, and JavaScripts for the web page designs. Avenue scripts are created to set up a map, update the data to the correct value for each day/data type, and export that map with the correct file name to the appropriate folder. So by executing one script, every image on the web site can be updated. The design of the web site using client-side JavaScript, however, is broken up into a few pieces that work together to make a complete package of tools for the user.

Figure 13:
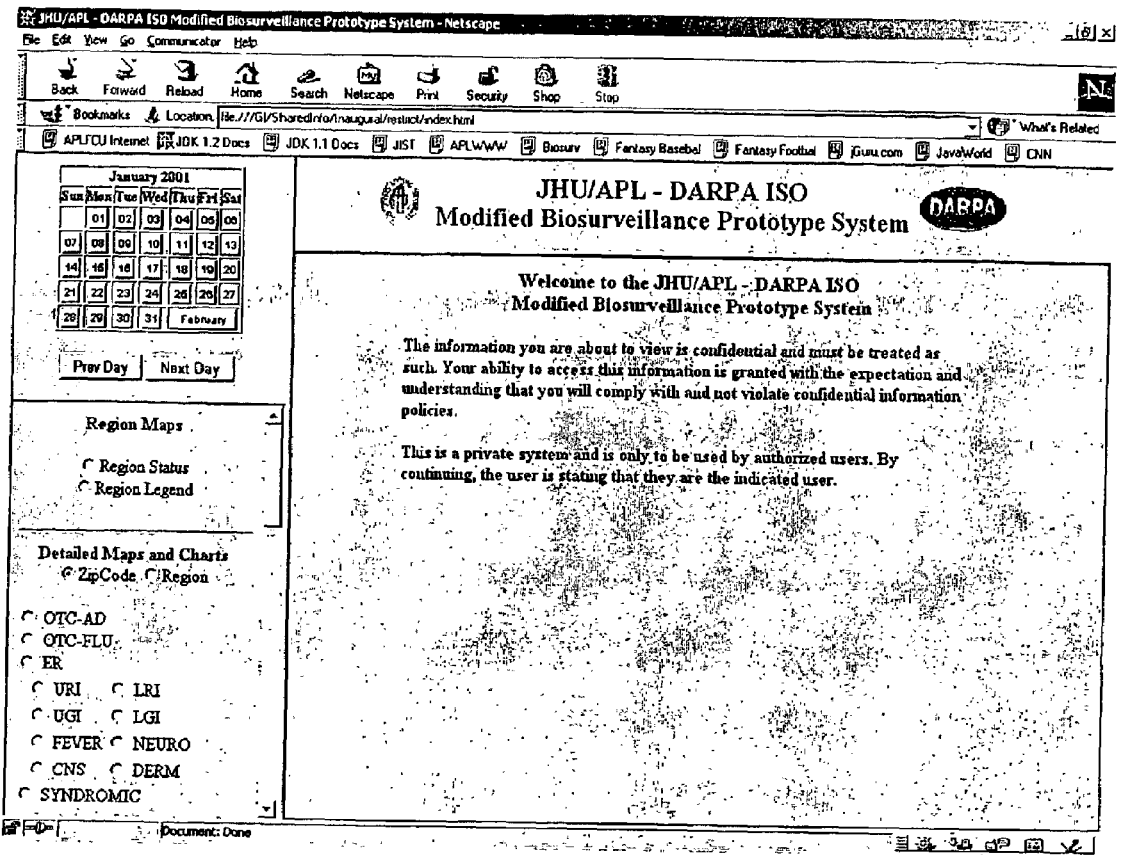
FIG. 13 shows a screen shot illustrating the first page of an on-line bio-surveillance system according to one example of the invention.

As an example, the design of one embodiment of the On-Line Bio-surveillance system is described in detail below. Upon visiting the web site, the user first sees the image shown in FIG. 13. In the upper-left corner is a calendar used for changing the date of the image a user wants to view. In the lower-left corner is the navigation bar used for choosing which data type to view. In the lower-right corner is the map area that starts initially with a splash screen of information, but is ultimately the area for viewing all maps and charts. And finally, in the upper-right corner is the title bar that displays logos and/or the title of a specific project. This frame-style design is used so the user always has simultaneous access to a calendar, navigation bar, title bar, and an image of interest.

The Calendar allows the user to quickly select a day for which the user wants to view data. This is done by clicking on a calendar date, or by using the "Prev Day"/"Next Day" buttons. The calendar modifies whatever map is currently open in the map area, to reflect the new date selected. If the calendar moves the date outside of a given range, it will automatically show an error page in the map area, telling the user they have selected an unavailable date.

The Calendar modifies the map page by using JavaScripting, and a variable passing technique that adds parameters to the end of the location URL for the map area. The "location URL" is the URL that a particular frame is pointed to at a particular time. Using JavaScript, the Calendar determines the location URL for the map area frame, and deciphers what type of page it is currently pointed to by parsing the URL. For example: https://secwww.jhuapl.edu/ncabiosurv/restrict/2001-01-01/maps.html?FLU_region. The Calendar would read that the current map is pointed to a region-based map of over-the-counter flu remedy sales for Jan. 1, 2001. To change the day, but keep the same type of page displayed, the Calendar simply changes the 2001-01-01 part of the URL to the correct day.

By using a separate frame for the title bar, every page is not required to reload the images and text each time a new page is viewed. This, in turn, speeds up the viewing speed. This also allows changing the title bar without modifying every other page on the site.

The Navigation Bar has several sections, which are displayed in FIG. 14. One section is the Region Maps section. It allows the user to view the Region Status and Region Legend maps. Once clicked on, the map area automatically changes to display the map of choice. This is done in this embodiment by using JavaScript. By using the "onClick" function, the radio buttons call JavaScript functions that parse the map area URL and change the end of the URL string to point to the correct type of map.

A next section of the navigation bar is the Detailed Maps and Charts section. Here the user can select from region or zip code based maps of each data type in the system. In the present embodiment, the data types include over-the-counter anti-diarrhea medication sales, over-the-counter flu remedy sales, emergency room data, and syndrome-based data. The emergency room and syndrome data are then broken up into subcategories for a more detailed picture. Again, once the radio buttons are clicked on, JavaScript is used to automatically change the map area to show the selected map.

Detector Outputs is another section of the navigation bar. This allows the user to select the regions of interest, and a disease of interest, and view the detector outputs in the map area Buttons for "check all" and "clear all" are used to allow the user to select or deselect each checkbox easily. After the user has selected appropriate checkboxes, the "get detector output" button is pressed, and a resulting JavaScript is then activated to change the map area to show each combination of region and disease selected.

The images are coded so that each region and disease correspond to a particular number code. For example, 01_01_mf.jpg is the image used to show the detector output for *Tularemia* in a particular region. This allows for the JavaScript to associate numbers with each checkbox, and simply combine the values of the selected checkboxes to get a filename for the image that needs to be displayed.

The Slide Show Control is also displayed on the navigation bar. This feature allows the user to select a data type and view all the images between two dates. The slide show control, like all other navigation pieces, operates by using form inputs and JavaScript. It uses the inputs from these form pieces to create a new URL for the map area to use. This URL passes parameters to the slideshow.html page, which then decodes the parameters and generates the slide show for a selected data type.

Still another section of the navigation bar informs the user of when the site was last modified, and gives contact information if the user has questions. This section of the navigation bar also uses JavaScript, as the date produced is written using a JavaScript to write out a data variable used throughout the system that contains the last modified date.

Figure 15A:
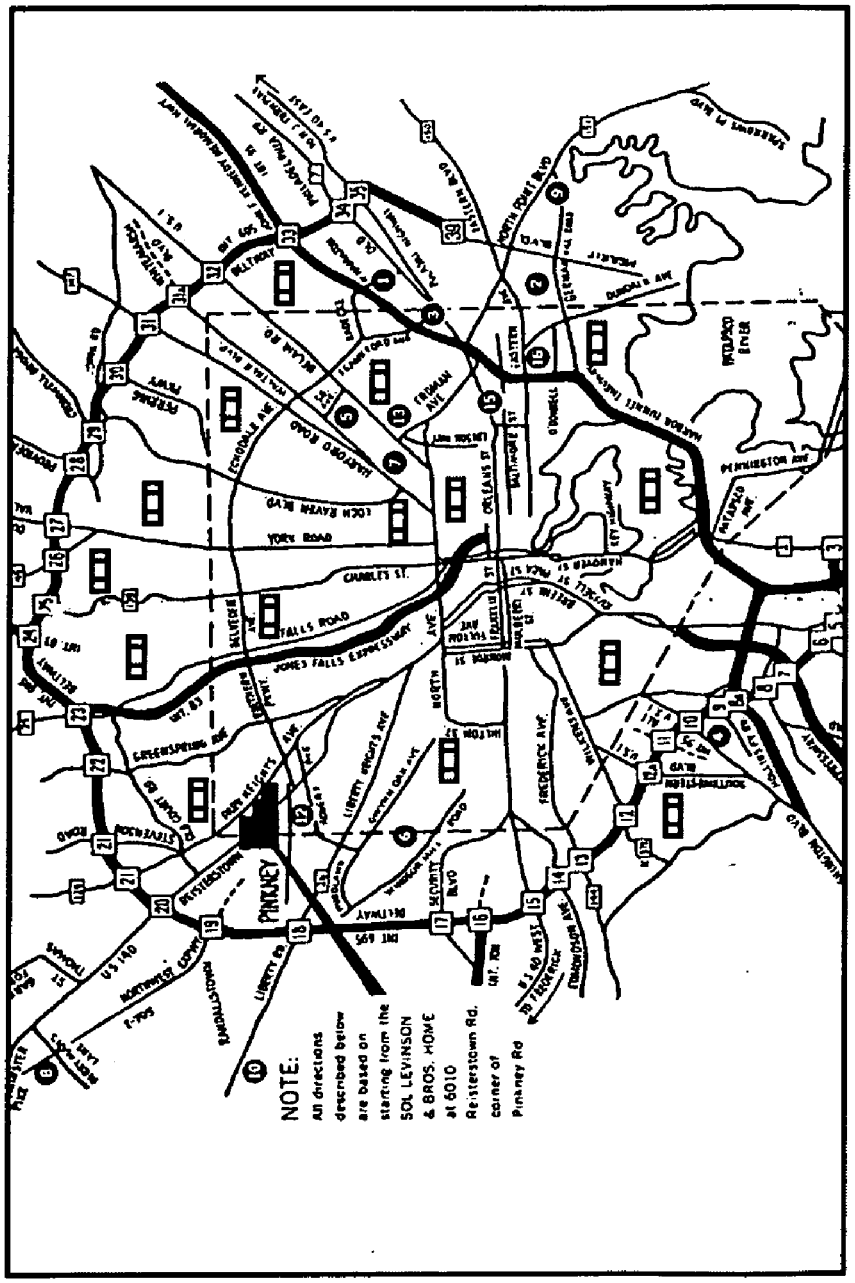
FIGS. 15A through 15C show screen shots illustrating various maps displayed in an on-line bio-surveillance system according to one example of the invention.
Figure 15B:
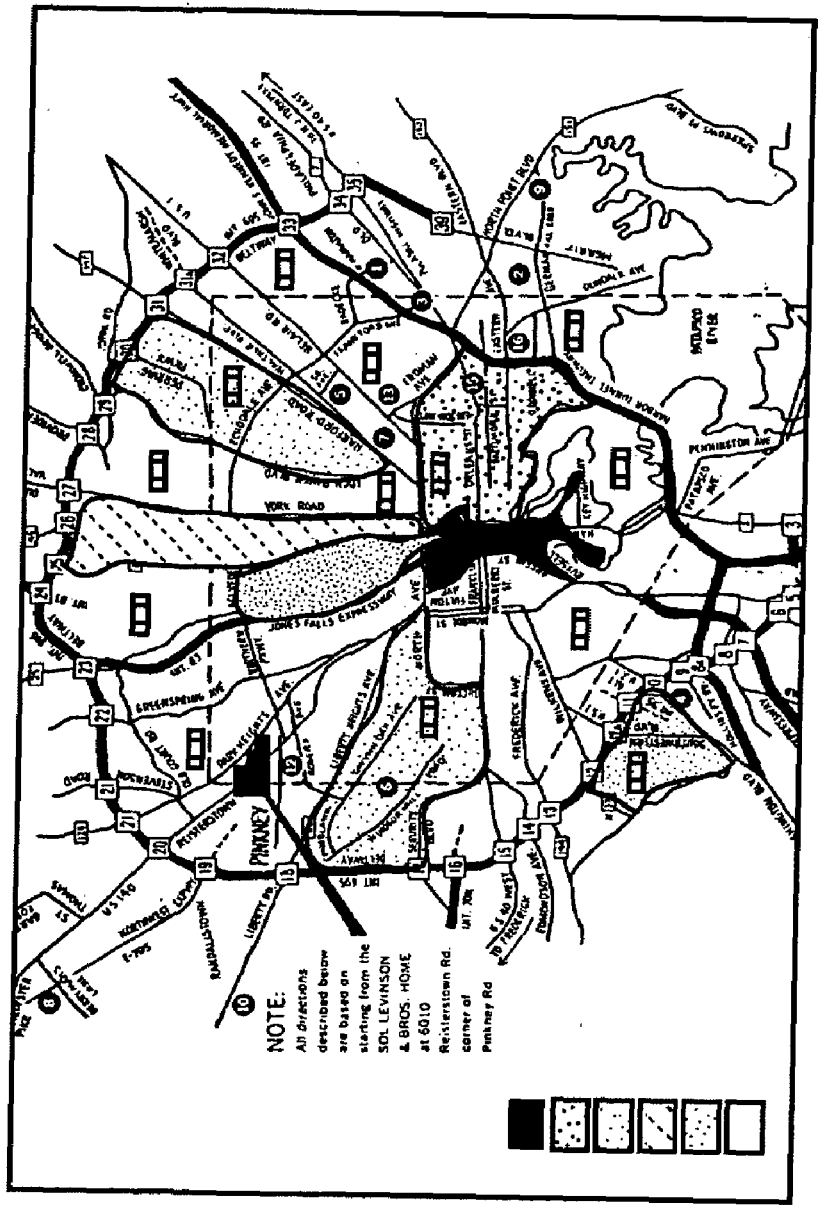
Figure 15C:
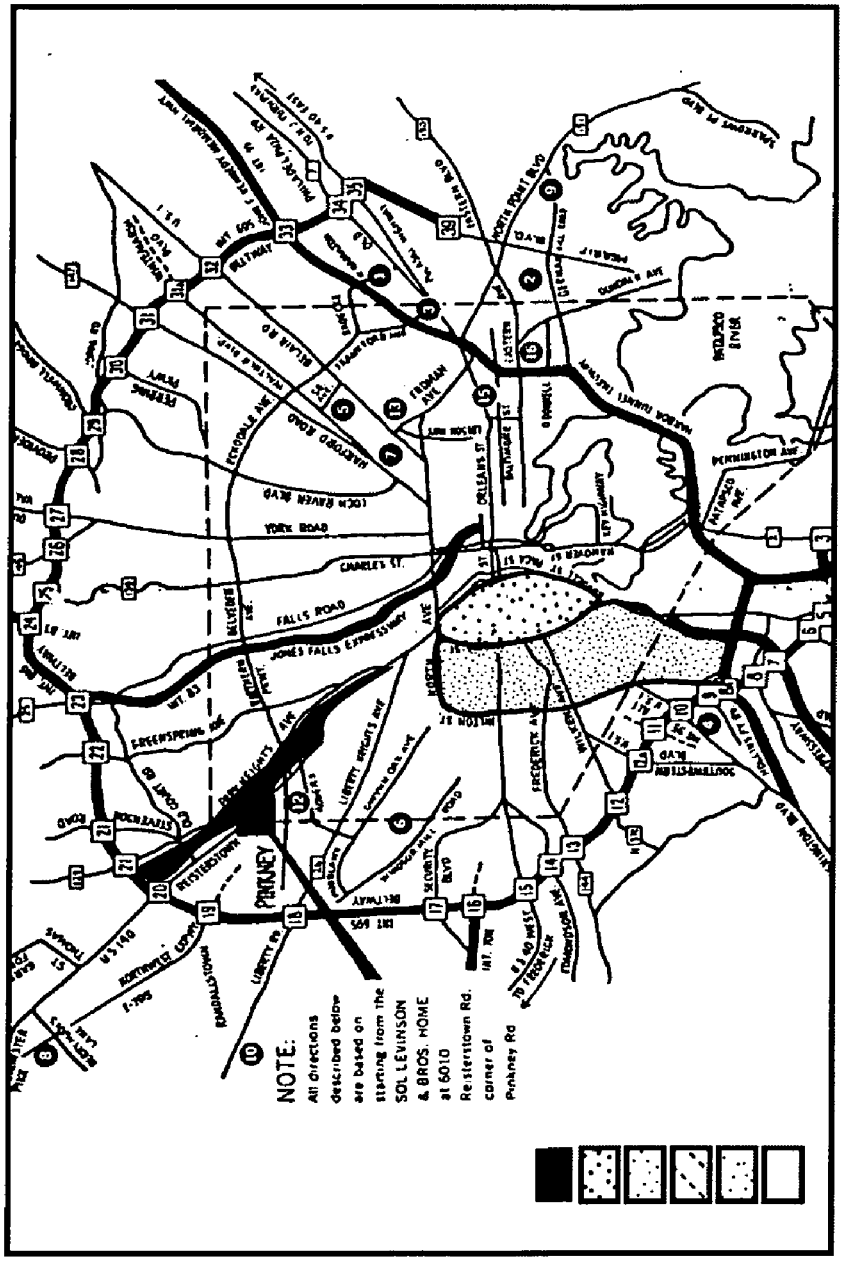

The map view area is where the maps, charts, and graphs are all displayed. This area is illustrated in FIGS. 15A-15C. Though it may display many different pictures, this area is actually controlled by only four html pages.

Maps.html takes inputs that produce region status maps (FIG. 15A), detailed zip code based maps (FIG. 15B), and detailed region-based maps (FIG. 15C). The URL that is given to the map area contains information about which type of map to display. For example, https://secwww.jhuapl.edu/ncabiosurv/restrict/2001-01-01/maps.html?FLU_region. From this URL a user can see that maps.html is called, and it is passed the variable "FLU_region". This instructs maps.html to display the region-based over-the-counter flu remedy sales map. The system also must label the map correctly with the date of the map, which is also decoded from the URL. Since all maps use the same level system for color-coding, only one static legend image is needed to describe the legend.

Having one html page to handle all these different data types and dates creates a larger html page (~64 Kb), but eliminates the need for over 40 different separate html pages to maintain per day. This feature of the system is very beneficial and allows for rapid changes to the system throughout the development process.

A special ability of the zip code based maps allows the user to determine the zip code pointed to on the map. An image map is added that places invisible circles onto the image. When a user's mouse pointer runs over each circle, the zip code they are pointing to will be displayed in the status bar at the bottom of the page. This image map information is created from an Avenue script that gets information from the zip code map in ArcView®.

Triggering an alert according to the present invention includes any standard method of notifying a system user that a detector threshold has been crossed. This includes simply issuing a warning when a threshold is crossed or displaying detector output images. Auto alerting could also be performed via page, e-mail, fax, or phone messages sent to disease control personnel for the jurisdictions where an abnormal condition exists.

Figure 16:
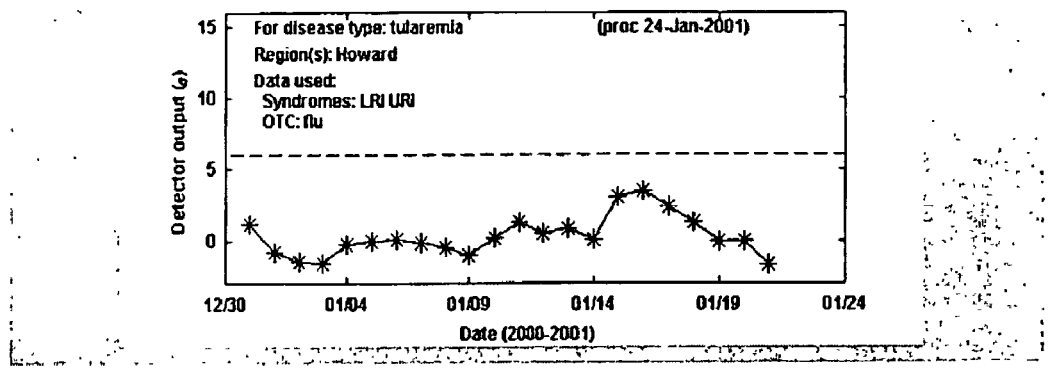
FIG. 16 shows a screen shot illustrating the detector output of an on-line bio-surveillance system according to one example of the invention.

An example of a detector output image is shown in FIG. 16. In the On-Line Bio-surveillance System, Detectors.html is the html page that deals with detector output images. Detector output images are different enough that they warrant a different html page from maps.html. Detectors.html, however, acts very similar to maps.html in that it reads parameters from its URL and uses those parameters to display the correct image. https://secwww.jhuapl.edu/ncabiosurv/restrict/2001-01-01/detectors.html?09_01&. This URL shows that detectors.html is called, and it is passed the parameter "09_01&". The "&" is there to separate multiple parameters, and the final "&" in the URL is ignored. The "09" tells the html page that it needs to display an image from a particular region. The "01" tells the html page that it needs to display a *Tularemia* image. The html page then puts the two together to display the "09_01_mf.jpg" image for the day to which the map area is currently pointed. If multiple parameters are passed, they are separated by the "&" and each image is displayed separated by a "<BR>" tag to stack the images on the page.

Figure 17:
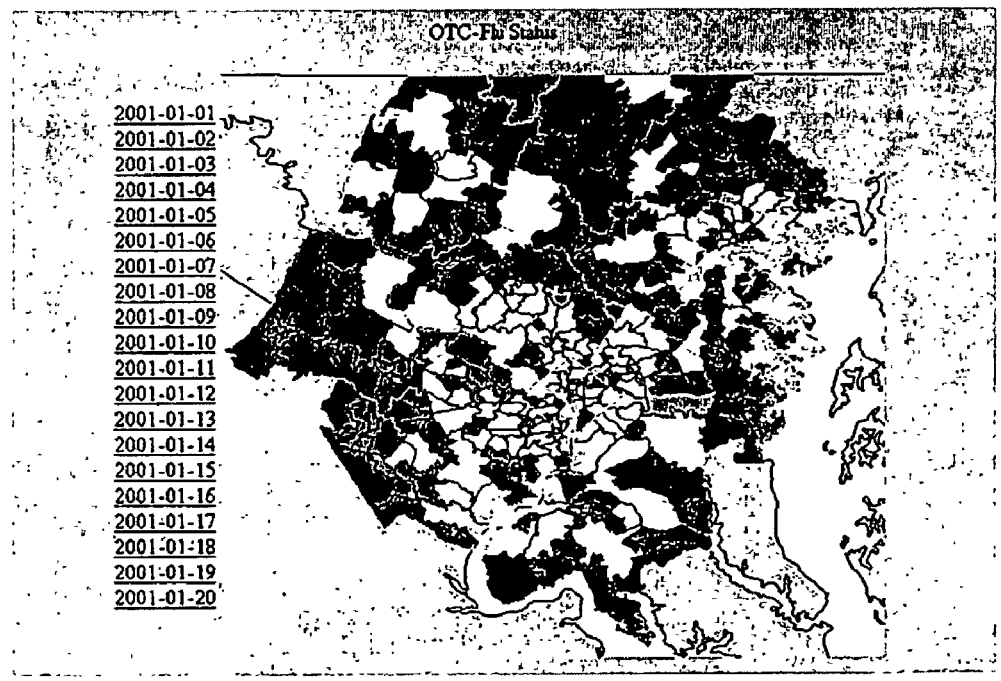
FIG. 17 shows a screen shot illustrating a slide show of an on-line bio-surveillance system according to one example of the invention.

The slideshow page is somewhat different from the two previous pages. An example of the slideshow page is shown in FIG. 17. The slideshow.html page is not located inside of a date folder, but in the main folder of the system. Because the slideshow is passed dates as parameters, there needs to only be one slideshow.html page, not one in each date folder.

The slideshow.html page takes in parameters similar to the previous html pages. https://secwww.jhuapl.edu/ncabiosurv/restrict/slideshow.html?FLU_zip&2001-01-01&2001-01-20. The "FLU_zip" tells the html page which data type to display. The "2001-01-01" tells the page when to start the slideshow, and the "2001-01-20" tells the page when to end the slideshow. After it receives the parameters, the page will begin to display the first image, and will begin downloading the rest of the images in the background. It also writes onto the screen a hyperlink for each date in the range. However, these hyperlinks are there not for the user to click on, but are there for the user to run their mouse over. Each hyperlink has an "onMouseOver" function attached to it. When the user runs their mouse over the link, it calls the "onMouseOver" function, which in turn calls other JavaScript functions that change the image the user can see on the page. It will change that image to the day the user's mouse has passed over. This allows the user to run their mouse up and down the date range, and watch how a data source changes throughout the range quickly and easily. If the user wishes to look at a particular date, they just hover the mouse over that day, and that day's image will stay on the screen. If the hyperlink is clicked, that particular image will be displayed in the map area all by itself. The user can then click the back button to get back to the slideshow.

The final html page that is used in the map region area is the region_legend.html page. This is a static page that shows the users what regions are used in the system. The term "region" is used instead of county, because the system maps all information to the zip code level. Zip codes do not map into counties cleanly, so the system considers the center point (as given by ArcView®) of each zip code, and uses that center point to determine what county each zip code is in. From there the system uses each of the zip codes in each county to outline a "region". This region is similar to the county, but follows the shape of the outer zip codes, and not the county.

Figure 18:
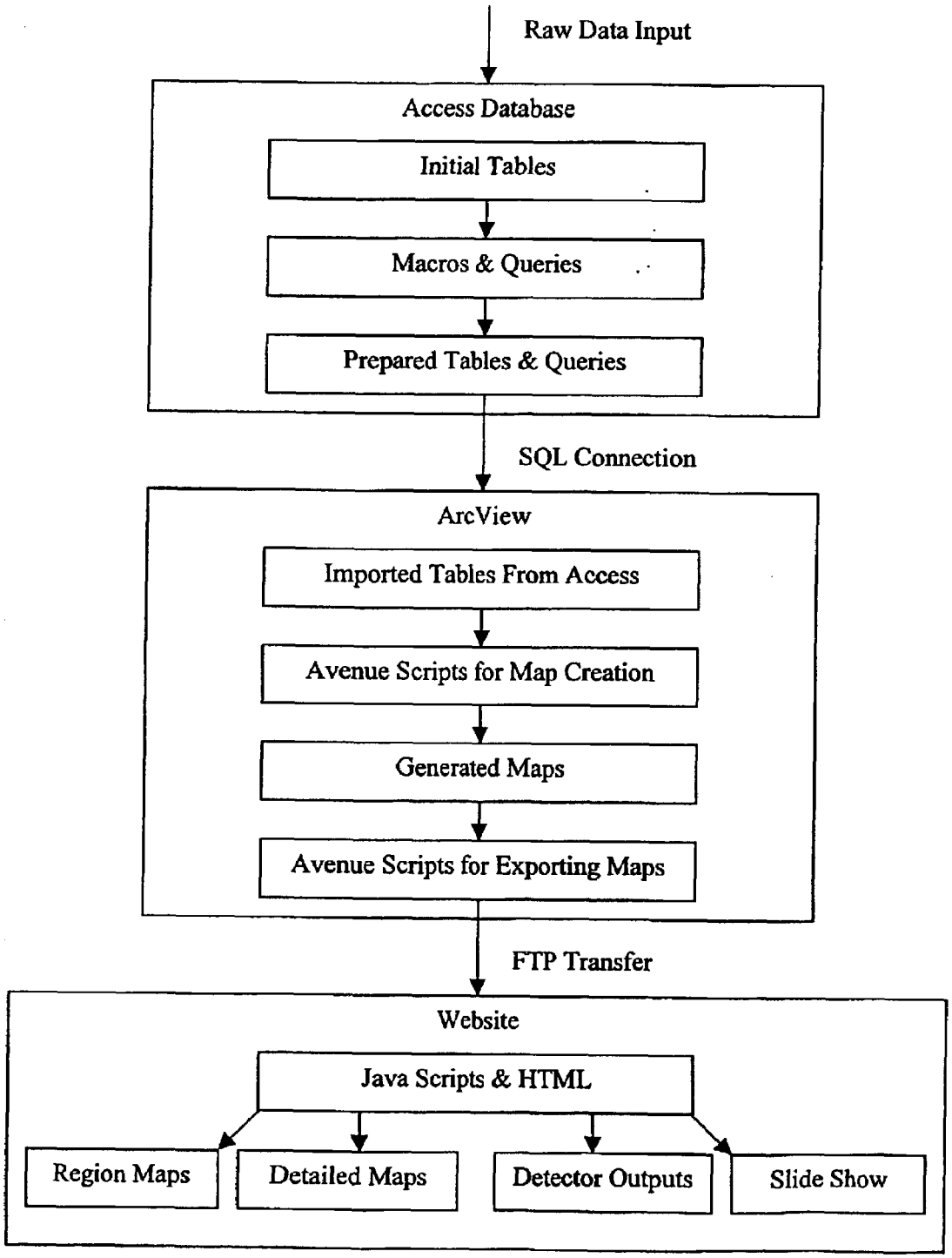
FIG. 18 is a data flow diagram illustrating the path of data through an on-line bio-surveillance system according to one example of the invention.

The Data Flow diagram shown in FIG. 18 illustrates the path of data through the system. It begins with raw data being added to the Access® Database. Raw data is initially placed into a set of tables and then is modified through a collection of macros and queries that populate a different set of tables. ArcView® then uses an SQL connection to query these new tables. It places a copy of the tables in ArcView®. Avenue scripts then generate a map for each data type and date based on the values in the tables. After generating each map, an Avenue script is called to export a JPEG image of the map into its correct place in the web site directory structure. Once all the images have been created, FTP is used to transfer the web site information to the secure web server. From the secure web site, users use different methods to view the maps and images including region and zip code based maps, detector output strip charts, and map slide shows.

When new data is added into the database, the following steps are used to update the website:
1) Open biowebsite.apr in ArcView®;
2) Point to ArcView_Inaugural.mdb;
3) Open the "dates_and_data" table, refresh it;
4) Open the "region_status_table" table, refresh it;
5) Open the "counts_by_zip_code" table, refresh it;
6) Open the "counts_by_region" table, refresh it;
7) Create new day folders as needed (e:/sharedinfo/inaugural/restrict/2001-01-01/), copy the "default_day" folder;
8) Modify and run the "Export All RegionStatus" script;
9) Run the "Export Zips and Regions" script (this will take ~1 hour);
10) Modify the lastUpdatedDate variables in the calendar and navigation html files;
11) Using windows explorer, right click on the restrict folder, and under the 7-Zip section, select "add to archive . . .";
12) Click "Ok" to begin creating a tar file called restrict.tar;
13) Telnet into aplcomm;
14) Change directory to /usr/local/share/opt/www/ncabiosurv/htdocs;
15) Remove the backup tar file;
16) Move the current restrict.tar to restrict.<date>.tar for a backup;
17) Use the "rm -R restrict" command to remove the current restrict directory;
18) FTP the newly made restrict.tar file into the current directory;
19) Use the "tar -xvf restrict.tar" command to untar the file;

In summary, the present invention is an automated system for detecting health events in populations that is designed to operate continuously and with minimal human intervention. It exploits modem information technology and advanced telecommunications to rapidly detect anomalies in monitored data, to compare such anomalies with multiple disease outbreak hypotheses, and to alert system users. Further, by monitoring numerous data sources simultaneously, the invention enables the detection of health events significantly in advance of other methods and systems that monitor a smaller number of data sources. The invention also enables a user to make additional inferences about the severity of a disease outbreak as well as its location, the nature of the disease, who is at risk, etc.

While the above description contains many specifics, the reader should not construe these as limitations on the scope of the invention, but merely as examples of specific embodiments thereof. Those skilled in the art will envision many other possible variations that are within its scope. Accordingly, the scope of the invention is determined by the appended claims and their legal equivalents, and not by the specific embodiments given above.

The invention claimed is:

1. A method for bio-surveillance detection and alerting, comprising the steps of:
   performing a center surround algorithm to create residual data related to population health, comprising
      computing background noise by averaging background data sets related to population health from different regions neighboring a center region, and
      subtracting said background noise from relevant data sets related to population health from the center region to create said residual data;
   modeling the effects of a hypothetical anomalous health-impacting event on said relevant data sets to create replica data of different types that simulates the effects of the anomalous health-impacting event on the relevant data sets;
   matching said residual data with said replica data using a detector to detect a real anomalous health-impacting event similar to said hypothetical health-impacting anomalous event; and
   triggering an alert if a real anomalous health-impacting event similar to said hypothetical anomalous health-impacting event is detected.

2. The method for bio-surveillance detection and alerting as recited in claim 1, wherein said background estimation algorithm includes a Kalman filter.

3. The method for bio-surveillance detection and alerting as recited in claim 1, wherein said detector is an adaptive matched-filter detector.

4. The method for bio-surveillance detection and alerting as recited in claim 1, wherein said detector is a Neyman-Pearson detector.

5. The method for bio-surveillance detection and alerting as recited in claim 1, wherein said detector is a change detector.

6. The method for bio-surveillance detection and alerting as recited in claim 1, wherein said detector includes a Bayesian Inference Network.

7. The method for bio-surveillance detection and alerting as recited in claim 1, wherein said relevant data sets comprise information on specific human behaviors exhibited during the onset of a disease.

8. The method for bio-surveillance detection and alerting as recited in claim 1, wherein said relevant data sets comprise over-the-counter drug sales data.

9. The method for bio-surveillance detection and alerting as recited in claim 1, wherein said relevant data sets comprise absenteeism data.

10. The method for bio-surveillance detection and alerting as recited in claim 1, wherein said relevant data sets comprise emergency room admissions data.

11. The method for bio-surveillance detection and alerting as recited in claim 1, wherein said relevant data sets comprise insurance claims billing data.

12. The method for bio-surveillance detection and alerting as recited in claim 1, wherein said relevant data sets comprise animal health data.

13. The method for bio-surveillance detection and alerting as recited in claim 1, wherein said relevant data sets comprise one or more of over-the-counter drug sales data, absenteeism data, emergency room admissions data, insurance claims billing data, and animal health data.

14. The method for bio-surveillance detection and alerting as recited in claim 1, wherein said relevant data sets comprise data from at least two different data sources.

15. The method for bio-surveillance detection and alerting as recited in claim 1, wherein said relevant data sets comprise data from at least five different simultaneous data sources.

16. The method for bio-surveillance detection and alerting as recited in claim 1, wherein said step of matching said residual data with said replica data uses more than one detector.

17. A method for bio-surveillance detection and alerting as recited in claim 1, further comprising the step of inputting information from a system user concerning a region of interest and a disease of interest.

18. A method for bio-surveillance detection and alerting as recited in claim 1, further comprising the step of sending an electronic message to disease control personnel in a jurisdiction where an alert has been triggered.

19. The method of claim 1, wherein:
said relevant data sets include data sets of different types;
said background data sets include data sets of different types corresponding to said different types of relevant data sets;
said subtracting step produces residual data of different types corresponding to said different types of relevant data sets;
said modeling step produces replica data of different types corresponding to said different types of relevant data sets; and
said matching step includes matching said residual date of different types with said replica data of different types.

20. The method of claim 1, wherein the replica data takes the form of an artificial signal having a magnitude proportional to a number of individuals in said population adversely affected by the health-impacting event, as indicated by said relevant data sets.

21. The method of claim 1, further comprising displaying via an internet web site said relevant data sets and said alert indicating said real anomalous health-impacting event.

22. A bio-surveillance detection and alerting system, comprising:
means for performing a center surround algorithm to create residual data related to population health, comprising
means for computing background noise by averaging background data sets related to population health from different regions neighboring a center region, and
means for subtracting said background noise from relevant data sets related to population health from the center region to create said residual data;
means for modeling the effects of a hypothetical anomalous health-impacting event on said relevant data sets to create replica data that simulates the effect of the anomalous health-impacting event on the relevant data sets; and
means for matching said residual data with said replica data to detect a real anomalous health-impacting event similar to said hypothetical health-impacting anomalous event; and
means for alerting a system user about said real anomalous health-impacting event.

* * * * *